US012377233B2

United States Patent
Von Blumenthal et al.

(10) Patent No.: US 12,377,233 B2
(45) Date of Patent: Aug. 5, 2025

(54) PROCESS AND DEVICES FOR AUTOMATICALLY SPECIFYING THE FREQUENCY SET POINT OF A VENTILATOR

(71) Applicant: Drägerwerk AG & Co. KGaA, Lübeck (DE)

(72) Inventors: Tilman Von Blumenthal, Lübeck (DE); Birgit Stender, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1007 days.

(21) Appl. No.: 17/466,787

(22) Filed: Sep. 3, 2021

(65) Prior Publication Data

US 2022/0072249 A1    Mar. 10, 2022

(30) Foreign Application Priority Data

Sep. 4, 2020   (DE) .......................... 102020123138.5

(51) Int. Cl.
  *A61M 16/00* (2006.01)
  *G16H 20/40* (2018.01)
  (Continued)

(52) U.S. Cl.
  CPC .......... *A61M 16/026* (2017.08); *G16H 20/40* (2018.01); *G16H 50/30* (2018.01); *G16H 50/50* (2018.01);
  (Continued)

(58) Field of Classification Search
  CPC ........ A61M 16/026; A61M 2205/3334; A61M 2230/46; A61M 16/0415; A61M 16/0461;
  (Continued)

(56) References Cited

U.S. PATENT DOCUMENTS

| 4,867,152 A | * | 9/1989 | Kou .......................... G06F 3/02 600/536 |
| 10,357,624 B2 | | 7/2019 | Van Der Staay et al. |

(Continued)

FOREIGN PATENT DOCUMENTS

| CN | 107257698 A | 10/2017 |
| CN | 109718440 A | 5/2019 |

(Continued)

OTHER PUBLICATIONS

Rees S E et al: "Using physiological models and decision theory for selecting appropriate ventilator settings", Journal of Clinical Monitoring and Computing, Springer Netherlands, NL, Bd. 20, Nr. 6, Sep. 15, 2006 (Sep. 15, 2006), XP037122867, ISSN: 1387-1307, DOI: 10.1007/S10877-006-9049-5.

(Continued)

*Primary Examiner* — Kendra D Carter
*Assistant Examiner* — Arielle Wolff
(74) *Attorney, Agent, or Firm* — McGlew and Tuttle, P.C.

(57) ABSTRACT

A process, a signal processing unit and to a ventilator automatically calculate a set point for a frequency, with which the ventilator performs ventilation strokes and thereby mechanically ventilates the patient. An alveolar or proximal minute volume is predefined. A lung time constant for the lungs of the patient is determined. The volume of a dead space in a fluid connection between the lungs and the ventilator is determined. A mandatory frequency set point ($f_{set,mand}$) for the mandatory ventilation of the patient is calculated. An ideal frequency ($f_{spon}$), with which the patient can achieve the minute volume by means of spontaneous breathing, is calculated. The ventilation frequency set point is calculated as a weighted average of the mandatory frequency set point ($f_{set,mand}$) and of the ideal frequency ($f_{spon}$).

(Continued)

The averaging depends on a determined actual intensity of the spontaneous breathing of the patient.

17 Claims, 8 Drawing Sheets

(51) Int. Cl.
*G16H 50/30* (2018.01)
*G16H 50/50* (2018.01)

(52) U.S. Cl.
CPC . *A61M 2205/3334* (2013.01); *A61M 2230/46* (2013.01)

(58) Field of Classification Search
CPC .. A61M 2016/0027; A61M 2016/0033; A61M 2205/502; A61M 2209/082; A61M 2209/084; A61M 2230/005; A61M 2230/04; A61M 2230/40; A61M 2230/42; A61M 2230/432; A61M 2230/60; A61M 16/024; A61M 16/0051; A61M 16/0069; A61M 2016/0036; A61M 2016/1025; A61M 2205/3344; A61M 2205/50; G16H 20/40; G16H 50/30; G16H 50/50; A61B 5/037; A61B 5/082; A61B 5/085; A61B 5/087; A61B 5/091; A61B 5/4836; A61B 5/08
See application file for complete search history.

(56) References Cited

U.S. PATENT DOCUMENTS

| | | |
|---|---|---|
| 2002/0020410 A1* | 2/2002 | Rydin ................ A61M 16/024 128/200.24 |
| 2004/0003813 A1 | 1/2004 | Banner et al. |
| 2008/0236582 A1 | 10/2008 | Tehrani |
| 2009/0007915 A1 | 1/2009 | Brunner et al. |
| 2009/0159082 A1 | 6/2009 | Eger |
| 2011/0017214 A1 | 1/2011 | Tehrani |
| 2012/0298108 A1 | 11/2012 | Kane et al. |
| 2016/0067434 A1 | 3/2016 | Schwaibold |
| 2018/0154095 A1* | 6/2018 | Van Der Staay . A61M 16/0051 |
| 2018/0221609 A1 | 8/2018 | Kühn et al. |
| 2019/0290867 A1 | 9/2019 | Van Der Staay et al. |

FOREIGN PATENT DOCUMENTS

| | | |
|---|---|---|
| EP | 2246087 A1 | 11/2010 |
| EP | 3332827 A1 | 6/2018 |
| WO | 2007131314 A1 | 11/2007 |
| WO | 2013027137 A1 | 2/2013 |
| WO | 2016178111 A1 | 11/2016 |

OTHER PUBLICATIONS

J. Mead: "Control of respiratory frequency," J. Appl. Physiol., vol. 15, No. 3, pp. 325-326, 1960.

J. Fernández, D. Miguelena, H. Mulett, J. Godoy, and F. Martinón-Torres, "Adaptive support ventilation: State of the art review," Indian J. Crit. Care Med., vol. 17, No. 1, p. 16, 2013.

\* cited by examiner

PROCESS AND DEVICES FOR AUTOMATICALLY SPECIFYING THE FREQUENCY SET POINT OF A VENTILATOR

CROSS REFERENCE TO RELATED APPLICATIONS

This application claims the benefit of priority under 35 U.S.C. § 119 of German Application 10 2020 123 138.5, filed Sep. 4, 2020, the entire contents of which are incorporated herein by reference.

TECHNICAL FIELD

The present invention pertains to a process and to a signal processing unit in order to automatically calculate a set point for the frequency, with which a ventilator performs ventilation strokes and as a result mechanically ventilates a patient. Furthermore, the present invention pertains to a ventilator, which automatically calculates a ventilation frequency set point for the ventilation strokes performed by the ventilator.

TECHNICAL BACKGROUND

A process and a device for calculating a ventilation frequency set point are described in EP 3 332 827 A1. The frequency, with which a patient shall be mechanically ventilated, is calculated automatically. The calculation depends on a desired minute volume (volume flow into and out of the lungs of the patient) as well as on a predefined functional dead space and, in addition, on a predefined lung model, on a stored lung time constant, e.g., R*C, and on a predefined duration ratio, e.g., inhalation I to exhalation E. The frequency is calculated such that a parameter depending on the frequency is minimized. In one exemplary embodiment this parameter is the sum of $W'_C$ and $W'_R$, i.e., the sum of the power $W'_C$ that is necessary for expanding the lungs and the power $W'_R$ that is necessary for overcoming the pneumatic resistance in the airway. An optimization, an iterative optimization in the exemplary embodiment, is carried out to specify the frequency set point.

A device and a process for automatically calculating a plurality of values for the parameters of a mechanical ventilation are described in US 2009/0 007 915 A1. A desired frequency $RR^{sp}$ of the ventilation is specified, and a frequency $RR_{spon}$ of the spontaneous breathing is determined. The two frequencies are compared with one another. A target value for the ventilation is specified as a function of the deviation. The target value may especially be the overall alveolar ventilation or the absolute or relative minute volume. In case the frequency of the spontaneous breathing deviates significantly from the frequency set point, then the target value for the ventilation is increased.

SUMMARY

A basic object of the present invention is to provide a process and a device, which automatically specify the ventilation frequency set point of a ventilator, wherein this specifying is valid for a relatively broad range of applications, and wherein it shall not be necessary to switch over the ventilator between different modes during the mechanical ventilation of a patient.

The object is accomplished by a process having features according to the invention, by a signal processing unit having features according to the invention and by a ventilator having features according to the invention. Advantageous embodiments are described. Advantageous embodiments of the process according to the present invention are, insofar as meaningful, also embodiments of the signal processing unit according to the present invention and of the ventilator according to the present invention and vice versa.

The term "intrinsic breathing activity" of the patient is used below. This intrinsic breathing activity is brought about by the patient's intrinsic respiratory muscles and may be caused by signals which are generated in the body of the patient (spontaneous breathing), and/or by signals which a medical device generates, to stimulate the intrinsic respiratory muscles of the patient from outside.

According to the invention, a fluid connection is established or can be established at least temporarily between the lungs of the patient, who is to be mechanically ventilated or who is being mechanically ventilated, and the ventilator. The ventilator is connected to a patient sensor configuration comprising at least one patient sensor or can at least temporarily be connected to a patient sensor configuration comprising at least one patient sensor. The patient sensor or each respective patient sensor (the patient sensor configuration) is capable of measuring at least one respiratory parameter of the patient to be ventilated or being mechanically ventilated.

The signal processing unit according to the present invention as well as the ventilator according to the present invention comprise a memory or the signal processing unit and the ventilator have read access to a memory at least from time to time. A value indicative of a desired volume flow into the lungs of the patient is stored on this memory in a form that can be analyzed by a computer. Such a desired volume flow value is predefined for the process according to the present invention.

A volume flow is the volume of fluid that flows into a space and/or out of a space, here: into and out of the lungs, within a defined time unit, e.g., in [L/min]. The desired volume flow is especially a required alveolar or proximal minute volume.

The process according to the present invention comprises the following steps carried out automatically, and the signal processing unit according to the present invention and the ventilator according to the present invention are configured and set up to automatically carry out the following steps:

A lung time constant for the lungs of the patient is determined. Measured values of at least one respiratory parameter of the patient, especially values from the patient sensor or from at least one patient sensor, are used for this determination.

The lung time constant τ s a parameter of the duration of the alveolar ventilation of the lungs. It depends on the elasticity and on the compliance of the lungs as follows: the greater the elasticity is and the greater the compliance is, the greater is the lung time constant. For example, the lung time constant τ s the product of the elasticity and the compliance. The lung time constant preferably indicates the time in seconds, after which two thirds of the breath volume are discharged from the lungs during exhalation, wherein the lungs are modelled as a linear pneumatic system. After three times of the lung time constant, 95% of the breath volume is discharged from the lungs.

The volume of a dead space is determined. This dead space is located in the fluid connection and between a region of the lungs that is suitable for the exchange of gases with the blood of the patient and the ventilator.

The dead space is preferably located between a measuring point at the mouth of the patient or in an area of the fluid connection, which is between the mouth and the ventilator, and the region of the lungs that is suitable for the exchange of gases.

A mandatory frequency set point for mandatory ventilation of the patient by means of the ventilator is calculated. This mandatory frequency set point is calculated as a function of the predefined desired volume flow, the determined lung time constant and the determined dead space volume. The desired volume flow into the lungs and out of the lungs of the patient can be achieved with this mandatory frequency set point solely by mechanical ventilation, i.e., without the intrinsic breathing activity of the patient contributing to this volume flow.

An ideal spontaneous breathing frequency for intrinsic breathing activity (spontaneous breathing and/or stimulated breathing) with the intrinsic respiratory muscles of the patient is calculated. With this ideal spontaneous breathing frequency, the patient is capable of achieving the desired volume flow, namely solely by intrinsic breathing activity. This ideal spontaneous breathing frequency is calculated as a function of the determined lung time constant and the determined dead space volume, preferably using a computer-analyzable mechanical lung model for the intrinsic breathing activity of a patient.

A value indicative of the current actual intensity of the intrinsic breathing activity of the patient is determined. This value indicates what absolute or relative contribution the intrinsic breathing activity of the patient makes to the overall ventilation of the lungs of the patient. If the intrinsic breathing activity of the patient is stimulated from outside, then the stimulated breathing activity likewise contributes to this value indicative of the current intensity. A mechanical ventilation performed by the ventilator makes the remaining contribution to the overall ventilation of the lungs.

The ventilation frequency set point to be specified is calculated as a weighted average of the mandatory frequency set point and the ideal spontaneous breathing frequency. What weighting, and especially what weight factor, is used in this weighted average, depends on the determined value indicative of the current actual intensity of the intrinsic breathing activity of the patient. The weight factor, with which the ideal spontaneous breathing frequency enters into the ventilation frequency set point, is preferably greater, the greater is the value indicative of the current actual intensity of the intrinsic breathing activity of the patient.

The ventilator is capable of performing ventilation strokes as a function of the calculated ventilation frequency set point, especially performing ventilation strokes with the calculated ventilation frequency set point.

According to the present invention, a ventilation frequency set point for the ventilator is automatically calculated. Hence, the present invention avoids the need to specify a ventilation frequency set point for a certain patient manually. The present invention also avoids the need to specify a ventilation frequency set point for a patient as a function of frequencies, with which patients were ventilated in the past. Rather, the ventilation frequency set point can be adapted to the patient who is currently to be ventilated and especially to the lungs thereof.

It is possible that the processing device (ventilator) is operated with this automatically calculated ventilation frequency set point, and especially performs ventilation strokes according to this automatically calculated ventilation frequency set point. It is preferably possible that the automatically calculated ventilation frequency set point is displayed or otherwise output to a user of the ventilator, and that an input of the user is detected and analyzed; it is especially detected whether the user confirms the displayed ventilation frequency set point or overwrites it with a different value. The ventilator then performs the ventilation strokes as a function of the ventilation frequency set point calculated according to the present invention and confirmed by the user or with a different ventilation frequency set point, which the user has entered.

According to the present invention, a value indicative of a desired volume flow into the lungs and out of the lungs of the patient is predefined, i.e., the volume of gas flowing into the lungs and the volume of gas flowing out of the lungs per time unit. The desired volume flow is preferably a desired alveolar or proximal minute volume. This desired volume is preferably the flow of volume into the region of the lungs and out of the region of the lungs that is available for the exchange of gases with the blood of the patient. The gases are especially breathing air, O2 and CO2 as well as optionally at least one anesthetic.

According to the present invention, a mandatory frequency set point for the mandatory ventilation of the patient as well as an ideal spontaneous breathing frequency of the intrinsic breathing activity of the patient are calculated. A mandatory ventilation is defined as the mechanical ventilation of a fully anesthetized patient, i.e., of a patient, who is currently not breathing spontaneously at all and whose respiratory muscles are also not externally stimulated. A mechanical ventilation with the mandatory frequency set point is capable of achieving the predefined desired volume flow, without the patient making a contribution to the ventilation of the lungs with the patient's own respiratory muscles. The patient is capable of generating the desired volume flow with the ideal spontaneous breathing frequency for the intrinsic breathing activity without a mechanical ventilation, wherein the ideal spontaneous breathing frequency preferably optimizes a predefined target function. The ideal spontaneous breathing frequency is preferably the frequency, with which the patient is capable of achieving the desired volume flow with the lowest mechanical work or with the lowest mechanical power, and especially preferably the frequency that leads to a minimal average mechanical power during inhalation (energy-efficient frequency).

The ventilation frequency set point is calculated according to the present invention as weighted sum, especially as weighted average, of the mandatory frequency set point and the ideal spontaneous breathing frequency for the intrinsic breathing activity. The ventilation frequency set point therefore depends on a weighting factor, wherein this weighting factor in turn depends on a determined value indicative of the current actual intensity of the intrinsic breathing activity of the patient. The greater this value indicative of the intrinsic breathing activity is and therefore the more intense the patient's intrinsic breathing activity is, the greater is the weighting factor and thus the contribution of the ideal spontaneous breathing frequency to the calculated ventilation frequency set point.

The feature according to the present invention that the weighted summary is calculated takes into account the fact that a patient is often not continuously fully anesthetized during the mechanical ventilation, but rather performs an intrinsic breathing activity at least from time to time, namely by spontaneous breathing and/or by externally stimulated breathing. The mechanical ventilation assists this intrinsic breathing activity of the patient P. The patient then breathes because of an overlap of the patient's intrinsic breathing activity and the mechanical ventilation. As a rule, the ventilator is configured or set so that a breath that is spontaneous or triggered by external stimulation triggers a ventilation stroke of the ventilator. In case of weak or absent intrinsic breathing activity, the ventilator performs additional ventilation strokes, i.e., some ventilation strokes that are not triggered by the intrinsic breathing activity. How many such additional ventilation strokes are performed depends on the ventilation frequency set point calculated according to the present invention and on the intrinsic breathing frequency of the patient. The risk that too few or too many ventilation strokes are performed, i.e., the patient receives too little or too much air or air at the wrong time, is reduced.

A mechanical ventilation may be a mandatory ventilation (patient performs no intrinsic breathing activity at all) or an assisted ventilation (mechanical ventilation assists the patient's intrinsic breathing activity). Thanks to the present invention, it is not necessary to switch over the ventilator between at least two different modes during the mechanical ventilation of a patient, namely at least one mode for the mandatory ventilation and at least one mode for the assisted ventilation. Such a switching over could lead to an abrupt change in the mechanical ventilation. Thanks to the present invention, the mechanical ventilation can rather be adapted to the current intensity of the intrinsic breathing activity, namely even if the desired volume flow remains the same and the intensity of the intrinsic breathing activity changes. The ventilation frequency can be changed gradually and needs not to be changed abruptly.

The calculated ventilation frequency set point according to the present invention can also be applied to the two special cases
    that the patient is fully anesthetized and
    that the ventilation strokes are triggered exclusively by the intrinsic breathing activity of the patient.

Thus, no ventilation stroke at all is triggered by the intrinsic breathing activity in the first case, and each ventilation stroke is triggered by the intrinsic breathing activity in the second case. Thanks to the present invention these two special cases do not necessarily have to be detected to specify the patient's ventilation frequency set point. It is sufficient to detect the value indicative of the patient's intrinsic breathing activity. The devices according to the present invention and the process according to the present invention can equally be used for the two special cases as well as for many intermediate situations between these two special cases, i.e., especially in case of a relatively weak intrinsic breathing activity.

The mandatory frequency set point is calculated according to the present invention as a function of the desired volume flow as well as the determined dead space volume and the determined lung time constant. The ideal spontaneous breathing frequency depends at least on the lung time constant c and on the dead space volume. For this reason, the calculated mandatory frequency set point depends on pneumatic properties of the lungs as well as on a desired volume flow into the lungs and out of the lungs. Hence, the mandatory frequency set point is adapted to the lungs of a patient to be mechanically ventilated. It is possible but not necessary to use a standard value or an average value, which is valid for a plurality of patients and therefore is not individually tailored to a patient.

The following two risks which may occur during mechanical ventilation are reduced since the lung time constant of the patient is determined and used according to the present invention:
    Because of a too high ventilation frequency, too little breathing air reaches the alveolar lung space. This adverse effect occurs especially in a lung with a high lung resistance (resistance) R and therefore with a large lung time constant $\tau$. In particular, the adverse situation may occur that too little used breathing air flows out of the lung during exhalation. The lung almost always continues to be inflated. This occurs, above all, in case of congested airways, especially in case of a smoker's lung.
    Because of a too low ventilation frequency, the lung is overstretched, especially because the achieved actual tidal volume is too high. This adverse effect occurs especially in case of a lung with a low elasticity (compliance) C and therefore with a short lung time constant $\tau c$.

For calculation of the mandatory frequency set point, the present invention makes it possible, but avoids the need, to determine the elasticity or compliance or pneumatic resistance of the lungs separately from one another. Such a determination is, in many cases not possible at all in practice, is prone to relatively large errors and/or burdens the patient considerably, especially when during ventilation at least one maneuver would have to be carried out for the determination. Thanks to the present invention, it is rather sufficient to determine a lung time constant.

The calculated ideal spontaneous breathing frequency for the intrinsic breathing activity of a patient also depends on the patient, namely on the determined dead space volume, which occurs in the body of the patient to a considerable extent and which may vary from patient to patient, as well as on the desired volume flow.

In one embodiment, the calculation of the ventilation frequency set point is carried out repeatedly for a patient, for example, when a predefined period of time has elapsed since the last calculation or the intrinsic breathing activity of the patient or a situation in the mechanical ventilation of the patient or a status of the patient has changed.

In a preferred embodiment, the mandatory frequency set point is calculated as a function of an ideal mandatory frequency set point and of an upper threshold for the mandatory frequency set point. The mandatory frequency set point is especially preferably equal to the ideal mandatory frequency set point or the upper threshold, depending on which of these two values is smaller.

The determined upper threshold for the mandatory frequency set point depends on the determined lung time constant and preferably additionally on the determined dead space volume and/or on the desired volume flow. The upper threshold may be the minimum of a plurality of individual upper thresholds, wherein a first individual upper threshold depends on the lung time constant and another individual upper threshold depends on the dead space volume and/or on the volume flow.

This embodiment makes it possible to take different constraints into consideration. Since the mandatory frequency set point is not greater than this upper threshold, the risk that the lungs will be too intensely mechanically stressed due to a too high frequency or due to a too high achieved tidal volume or do not receive sufficient breathing air is further reduced. It is especially avoided that the mechanical ventilation due to a too high frequency mainly moves breathing air through the dead space in both directions, without a sufficient quantity of breathing air reaching the region of the lung that is suitable for the exchange of gases and without a sufficient quantity of used air being discharged out of the lungs.

However, if the upper threshold would always be used as the mandatory frequency set point, then there would be a risk that the lungs will be mechanically stressed due to the mechanical ventilation more intensely, i.e., more intensely than necessary in order to achieve the desired volume flow. Hence, the mandatory frequency set point may be smaller than the upper threshold, namely especially equal to a calculated ideal mandatory frequency set point.

The ideal mandatory frequency set point is, in one embodiment, calculated as a function of a predefined required inhalation portion. The inhalation portion predefines a value indicative of the time share an inhalation process has, on average, in a breathing cycle. It is possible to predefine the ratio between the average duration of an inhalation process and the average duration of an exhalation process. It is also possible to predefine the average duration of an inhalation process or the average duration of an exhalation process. The duration of the inhalation process or exhalation process as well as the ventilation frequency specify an inhalation portion.

In a preferred embodiment, a lung model in a form that can be analyzed by a computer is predefined and stored in the memory and is used to calculate the ideal mandatory frequency set point. This lung model describes approximately the pneumatic behavior of the lungs of a person and thus also of the lungs of a mechanically ventilated patient. This lung model preferably contains at least one model parameter, especially the lung time constant and/or the dead space volume. The respective value of the model parameter or of each model parameter may vary from patient to patient. Using this lung model, it is possible to automatically predict what resistive power and what elastic power act on the lungs. The ideal mandatory frequency set point is calculated using the predefined lung model and the predefined inhalation portion.

A resistive power and an elastic power are calculated using the predefined lung model and the required inhalation portion. The resistive power is the work per time unit that is to be applied during an inhalation process in order to overcome the pneumatic resistance of the lungs. The elastic power is the work per time unit that is to be applied in order to expand the lungs. It is predicted what frequency leads to what resistive power and to what elastic power according to the lung model and in case of the predefined inhalation portion in order to calculate the ideal mandatory frequency set point.

In an especially preferred embodiment, this ideal mandatory frequency set point is specified such that the resistive power brought about differs from the elastic power brought about by a predefined power factor at most, wherein the power factor is preferably the quotient of the two mechanical powers brought about. The power factor can be selected to be so small that the resistive power is greater, but only slightly greater than the elastic power, preferably at most 20% greater. The power factor can be predefined beforehand. This embodiment leads in many cases to a relatively low mechanical stress on the lungs, especially because each tidal volume achieved is relatively small. Yet, the embodiment brings about a sufficiently large volume flow into the lung region and out of the lung region suitable for the exchange of gases, especially the alveolar lung space.

The advantageous embodiment with the power factor avoids the need to minimize a function that describes the overall mechanical work or the overall power, which acts on the lungs during the mechanical ventilation. The need is especially avoided to minimize such a function during run time, i.e., during the mechanical ventilation. The minimization of a function is time-consuming and requires a relatively large computing capacity. If an iterative process is used in the minimization and if the process is interrupted at the run time when an interruption criterion is met, then the minimization may lead to an unfavorable result. Without a suitable interruption criterion, the minimization may last too long. The advantageous embodiment avoids the drawbacks of such a minimization at the run time.

In a preferred embodiment, an initialization phase and a subsequent use phase are carried out for the mechanical ventilation of the patient. A constant $\tau$ s calculated in the initialization phase. In order to calculate the constant, the lung model and preferably the optionally predefined power factor are used. The ideal mandatory frequency set point is calculated in the subsequent use phase. The inhalation portion, the lung time constant determined for the patient as well as the constant, which was calculated in the initialization phase, are used for this calculation. This embodiment frequently leads to a lower computing effort in the use phase. It is possible to calculate the constant again in the use phase, for example, because of a changed specification for the mechanical ventilation. It is possible to use the results of the initialization phase for a plurality of patients during the use phase and the calculations are carried out again in this use phase for each patient and therefore lead to results which are specific to the patient.

In a variation of this embodiment, a first signal processing unit calculates the constant $\tau$ n the initialization phase. A second signal processing unit calculates the ideal mandatory frequency set point and the ventilation frequency set point in the use phase from this ideal mandatory frequency set point. The first signal process unit is not necessarily a component of the ventilator.

According to a just described embodiment, an ideal mandatory frequency set point is calculated as a function of a predefined required inhalation portion. The greater the predefined required inhalation portion is, the greater is the ideal mandatory frequency set point.

According to the present invention, a mandatory frequency set point for the mandatory ventilation of the patient as well as an ideal spontaneous breathing frequency for the intrinsic breathing activity of the patient are calculated. The mandatory frequency set point is preferably calculated such that it is greater than or equal to the ideal spontaneous breathing frequency. The specified ventilation frequency set point is then also at least as high as the ideal spontaneous breathing frequency. As a result, a too low ventilation frequency is avoided. It is especially ensured that at least each spontaneous breath or externally stimulated breath of the patient triggers a ventilation stroke. It is possible that at least one ventilation stroke is performed, which is not triggered by a spontaneous or stimulated breath of the patient.

A ventilation frequency set point is calculated according to the present invention. An operating parameter, which is frequently set at a ventilator, is a required tidal volume. This required tidal volume is a parameter corresponding with a required volume, which the ventilator shall feed into the fluid connection during a single ventilation stroke. In one embodiment of the present invention, the required tidal volume is calculated as a function of the desired volume flow, the determined dead space volume and the ventilation frequency set point calculated according to the present invention. The ventilator is actuated with the control target that the tidal volume that is actually achieved during at least one ventilation stroke is equal to the calculated set tidal volume. In each ventilation stroke during the mechanical ventilation, the actual tidal volume shall preferably be equal to the set tidal volume, at least until a new set tidal volume is calculated and predefined. An actuator of the ventilator is preferably actuated depending on the set tidal volume. Preferably a control is carried out, in which the control target is that the actual tidal volume is equal to the set tidal volume. During each ventilation stroke being carried out after the ventilation frequency set point is calculated and until a new set point is calculated or until the mechanical ventilation is completed, the achieved actual tidal volume shall preferably be equal to the calculated set tidal volume.

The ventilator feeds fluid into the fluid connection during a ventilation stroke. The pressure at a measuring point in the fluid connection increases until the pressure has reached a maximum value. In one embodiment, the actually achieved pressure is regulated or controlled, wherein a time course (time curve) of the required pressure is predefined and wherein the ventilator is actuated with the control target that the actual time course of the pressure at the measuring point is equal to the predefined time course. A control is preferably carried out with the control target that the actual pressure curve is equal to the set pressure curve.

If the predefined time course of the pressure reaches the maximum value abruptly, then there is a risk that the lungs of the patient will be damaged. Hence, a required ramp time is preferably calculated for at least one ventilation stroke, preferably for each ventilation stroke. In the required time course of the pressure, this set ramp time specifies the required period of time which shall elapse between the beginning of a ventilation stroke and the time, at which the maximum value of the pressure is reached.

The regulation or control of the actual pressure time course is carried out with the control target that the ramp time that is actually achieved is equal to the calculated set ramp time. This set ramp time is preferably used for the ventilation stroke carried out until a ventilation frequency set point is calculated again or until the mechanical ventilation is completed.

The set ramp time is preferably calculated as a function of the determined lung time constant of the patient. It is also possible to use an ideal body weight of the patient in addition to the lung time constant or instead of the lung time constant. This ideal body weight can be deduced from easily measurable parameters of the patient.

According to the invention a dead space volume in the fluid connection is calculated. A main share of this dead space occurs in the patient's body between the mouth and those parts of the lungs which can exchange O2 and CO2 between inhaled air and the body. In one embodiment the volume flow out of the lungs is measured, i.e. the exhaled air during one breath. The time span in which the exhaled air does not contain a relevant CO2 share is determined. The volume flow and the time span together yield an estimation for the dead space volume. The background: The dead space cannot add CO2 to the exhaled air. In a simple alternative the dead space volume is roughly estimated by using a standard value or depending on the patient's ideal or actual body weight. Other ways of determining the dead space volume are also possible.

The present invention will be described below on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

In an exemplary embodiment, the present invention is used to mechanically ventilate a patient. A fluid connection is established between the lungs of the patient and a ventilator. Breathing air or another gas mixture is fed to the patient through this fluid connection. Optionally, this gas mixture is mixed with at least one anesthetic, so that the patient is partially or fully anesthetized. The fluid connection optionally belongs to a ventilation circuit that receives the exhaled air again, especially when an anesthetic is added. In case of a ventilation circuit, the ventilator filters carbon dioxide (CO2), optionally also the anesthetic or each anesthetic, out of the exhaled breathing air.

Figure 1:
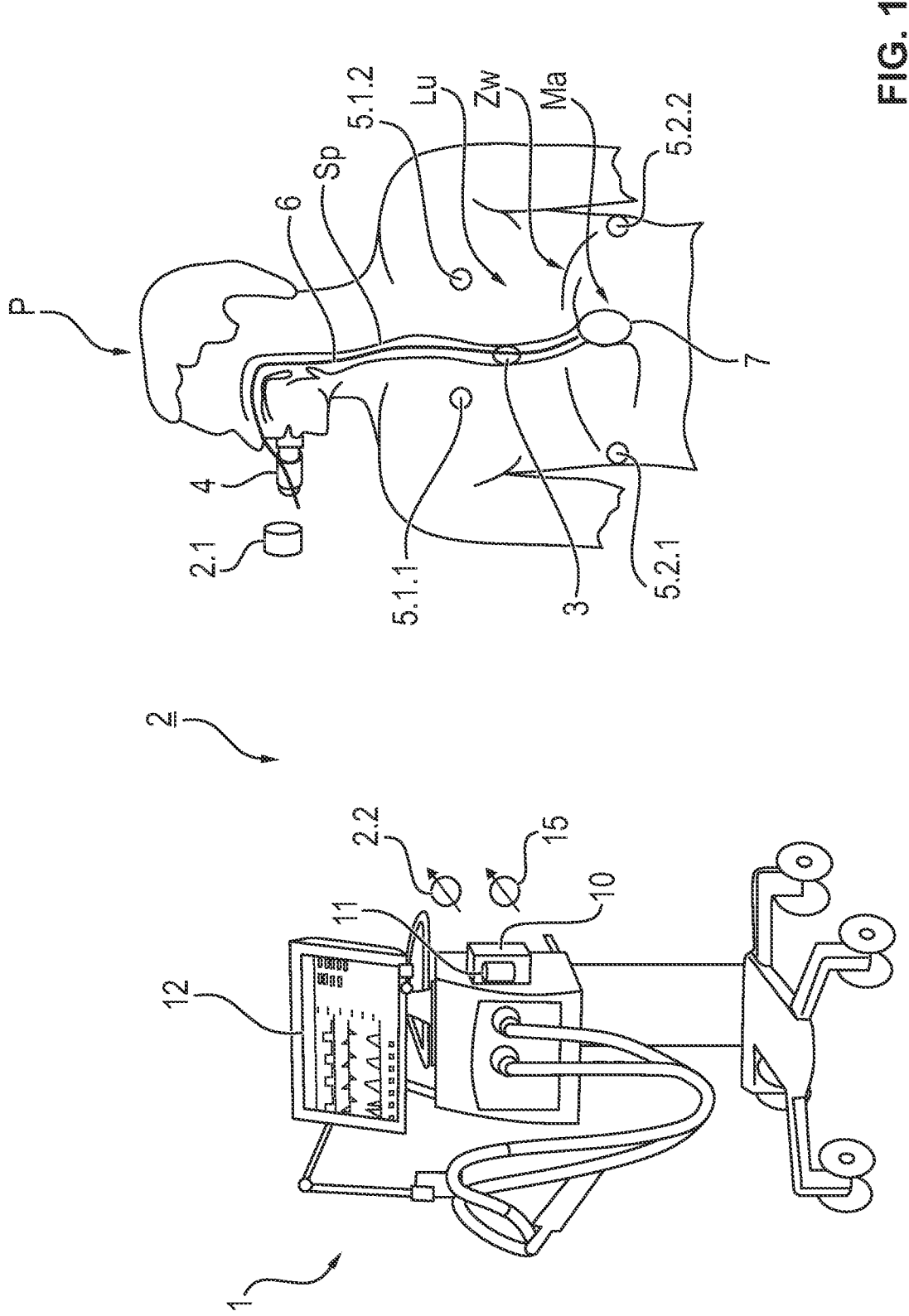
FIG. 1 is schematic view showing in an exemplary manner a mechanically ventilated patient, a ventilator as well as a plurality of sensors.

FIG. 1 shows in an exemplary manner a patient P, who is mechanically ventilated. The lungs Lu, the esophagus Sp, the stomach Ma and the diaphragm Zw of the patient P are shown schematically. A ventilator 1 with a display and operating unit 12 as well as with a data processing signal processing unit 10 ventilates the patient P mechanically. The signal processing unit 10 comprises a processor configuration comprising at least one processor, and a memory (or access to a memory) 11. The ventilation tubes between the ventilator 1 and the patient P are not shown. A flexible connection piece 4 is located in the mouth of the patient P during ventilation. In one embodiment, a flexible measuring catheter 6 is placed into the esophagus of the patient P, wherein the measuring catheter 6 begins in the connection piece 4.

Different sensors measure different pneumatic vital parameters of the patient P and/or parameters of the fluid connection between the ventilator 1 and the lungs Lu of the patient P. In order to carry out the present invention, all these sensors do not necessarily have to be present. The following sensors are shown in FIG. 1:

A pneumatic sensor 2 comprises a transducer 2.1 comprising an opening, which is arranged in the vicinity of the mouth of the patient P and taps air from the fluid connection. The tapped air is transmitted via a hose, not shown, to a pressure sensor 2.2, which measures a value indicative of the airway pressure $P_{aw}$ (pressure in airway) in the fluid connection and optionally a value indicative of the volume flow (volume rate of flow) Vol'. In one embodiment the transducer 2.1 is arranged in or at a Y-piece close to the connection piece 4, i.e., close to the mouth of the patient P.

Optionally, a sensor 15 in or at the ventilator 1 measures a value indicative of the volume Vol' per time unit of the breathing air flow from the ventilator 1 to the patient P (e.g., inspiratory minute volume) and/or back from the patient P to the ventilator 1 (e.g., expiratory minute volume).

A probe 3 in the esophagus Sp of the patient P, preferably comprising a measuring balloon, measures a value indicative of the pneumatic pressure $P_{es}$ (pressure in esophagus), which is variable over time, in the esophagus Sp. The probe 3 is in a fluid connection with the connection piece 4 via the measuring catheter 6 or is a part of the measuring catheter 6.

An additional measuring balloon of the probe 3 or an optional gastric probe 7 in the form of a measuring balloon, which is placed into the stomach Ma, measures a value indicative of the gastric pressure $P_{ga}$ in the stomach Ma.

A plurality of measuring electrodes are attached to the chest of the patient P. FIG. 1 shows a pericardial pair 5.1.1, 5.1.2 of measuring electrodes and a peridiaphragmatic pair 5.2.1, 5.2.2 of measuring electrodes as examples. An electrocardiogram (EKG) and/or an electromyogram (EMG) of the patient P are generated by means of these optional measuring electrodes 5.1.1, ..., 5.2.2 as well as by a measuring electrode for electrical ground, not shown.

The signal processing unit 10 is capable of automatically determining when air or another gas mixture flows into the breathing system of the patient P and when the gas mixture again flows out of the breathing system, i.e., is capable of detecting each inhalation phase and each exhalation phase. For this, the signal processing unit 10 uses measured values from the sensors 2, 3, 7 and 15 and optionally from the measuring electrodes 5.1.1 through 5.2.2.

In one application, the patient is fully anesthetized and is not performing any intrinsic breathing activity, i.e., the patient does not carry out any spontaneous breaths at all or at most some spontaneous breaths, and the patient's respiratory muscles are also not stimulated externally. The ventilator 1 carries out a mandatory ventilation in this application. In another embodiment, the patient P breathes spontaneously at least from time to time, and the patient's respiratory muscles are optionally stimulated externally. The ventilator 1 assists the intrinsic breathing activity of the patient P by the ventilator 1 delivering a gas mixture into the lungs. Temporal transitions between these two ventilation modes are also possible.

In both modes of ventilation, the ventilator 1 performs a series of ventilation strokes. The ventilator 1 feeds breathing air or another gas mixture into the fluid connection during each ventilation stroke. The mechanical ventilation is characterized by a plurality of pneumatic operating parameters, among others a required time course of the pressure, which the ventilation 1 generates during the ventilation strokes, a required time course of the volume of the gas mixture, which is fed into the fluid connection during the ventilation strokes, a frequency of the ventilation strokes or even the amplitude, i.e., the maximum pressure difference during the ventilation strokes.

A person takes in air or another gas mixture with the intrinsic respiratory muscles in a spontaneous or stimulated breathing or with the mechanical ventilation, which is carried out with a frequency $f_{ist}$, wherein this gas mixture of oxygen and optionally at least one anesthetic, which is taken in with a breath, is designated as (actual) breath volume or tidal volume $Vol_{Tid,ist}$. The alveolar lung space is available for the exchange of oxygen and carbon dioxide between the fed gas mixture and the blood. The volume of gas, which actually flows through the alveolar lung space, is designated below as the "achieved alveolar lung volume." The process of gas flowing through the alveolar lung space is often designated as "alveolar ventilation." A dead space with the overall volume $V_D$ occurs in the upper airway and middle airway of the patient P in a region of the lungs Lu, in which no gas is exchanged with the blood, as well as—in case of a mechanical ventilation—in the area of the fluid connection, through which the air or gas mixture flows in both directions, wherein the gas flows through this dead space in both directions, but is not available for the exchange of oxygen and carbon dioxide. The achieved alveolar lung volume per time unit, in [L/min] in the exemplary embodiment, is designated as the actual alveolar minute volume $V'_{A,ist}$. Then $$V'_{A,ist} = f_{ist} * (Vol_{Tid,ist} - V_D) \quad (1)$$

applies. The actual alveolar minute volume $Vol'_{A,ist}$ correlates with the volume flow Vol', which is measured at a measuring point, for example, by means of the transducer 2.1 and the pressure sensor 2.2. A dead space, in which no gas exchange takes place, occurs in the fluid connection between the ventilator 1 and the lungs Lu of the patient P. Only the device-side dead space, which is located between the measuring point 2.1 and the patient P and through which gas flows in both directions, is to be taken into consideration. In many cases, this device-side dead space has a negligibly small volume $V_{D,Ger}$, so that only the volume $V_{D,Pat}$ of the patient-side dead space is used as the overall volume $V_D$.

A desired alveolar minute volume, which is the volume per time unit of the gas mixture that flows through the alveolar lung space and is therefore available for the exchange of oxygen and carbon dioxide with the blood of the patient P, is predefined in the exemplary embodiment. This minute volume is indicated, for example, in liters per minute and is designated by $V'_{A,req}$. This desired alveolar minute volume $V'_{A,req}$ is predefined, especially by a user by means of the display and operating unit 12 at the ventilator 1 or is automatically set. In one embodiment, the desired alveolar minute volume $V'_{A,req}$ is deduced automatically or by a user, for example, as a function of a required time course of the CO2 content in the exhaled breathing air. Such a time course is also designated as a capnogram or capnography curve and can be measured by means of a CO2 sensor.

Instead of a desired alveolar minute volume $V'_{A,req}$, a desired proximal minute volume can also be predefined. The actual proximal minute volume $V'_{P,ist}$ is the volume flow at the mouth of the patient P, especially the volume flow at a tube connector.

The volume flow is split up into the alveolar air stream and the flow through the dead space. The volume $V_{D,Ger}$ of the device-side dead space is negligibly small at a measured point at the patient P or close to the patient P. The actual proximal minute volume $V'_{P,ist}$ is connected with the actual alveolar minute volume $V'_{A,ist}$ as follows:

$$V'_{P,ist} = V'_{A,ist} + V_D * f_{ist} = V'_{A,ist} + (V_{D,Pat} + V_{D,Ger}) * f_{ist} \quad (2)$$

Herein, $V_D$ is the entire volume of the dead space, which in the exemplary embodiment is equal to the sum of the volume $V_{D,Pat}$ of the patient-side dead space and the volume $V_{D,Ger}$ of the device-side dead space, and $f_{ist}$ is the actual ventilation frequency of the ventilator 1. This device-side volume $V_{D,Ger}$ is, as a rule, known because of the construction of the ventilator 1 and the hoses of the fluid connection and can in many cases be disregarded.

For example, the desired alveolar minute volume $V'_{A,req}$ or the desired proximal minute volume $V'_{P,req}$ is predefined such that desired values for the concentration or for the partial pressure of certain gases in the blood of the patient P are achieved as well as possible. The minute volume $V'_{A,req}$, $V'_{P,req}$ can be predefined by a user or by a higher-level automation system or is permanently stored in the memory 11 of the ventilator 1.

According to the present invention, the signal processing unit 10 automatically calculates a ventilation frequency set point $f_{set}$ of the ventilator 1, namely as a function of a desired alveolar minute volume $V'_{A,req}$. The signal processing unit 10 preferably receives measured values from the sensors 2, 3, 5.1.1, . . . , 5.2.2, 7 and carries out the necessary calculation steps as a function of the measured values received. In one embodiment, this calculation is carried out repeatedly at fixed time intervals or in case of a triggering event, for example, in case of a change in the status of the patient P.

The calculated ventilation frequency set point $f_{set}$ is used in the exemplary embodiment in a lower-level control for the pressure. The actually achieved pressure is the controlled variable and is measured, preferably as the achieved airway pressure $P_{aw}$. A desired time course $P_{set}$ of the pressure is predefined as a command variable. The calculated ventilation frequency set point $f_{set}$ determines the frequency of the pressure increases and thus of the ventilation strokes in this desired time course of $P_{set}$.

A lower-level control device, not shown, brings about that a final control element of the ventilator 1 is actuated, and this final control element generates the ventilation strokes. As a rule, the actually achieved ventilation frequency $f_{ist}$ is equal to the automatically calculated ventilation frequency set point $f_{set}$. Nevertheless, different designations are used below for illustration.

A frequency set point is predefined in case of a mandatory ventilation, while the frequency depends on the intrinsic breathing activity of the patient P and therefore may vary in case of assisted ventilation. How the ventilation frequency set point is calculated for a mandatory ventilation is first described below. This mandatory ventilation frequency set point is designated below by $f_{set,mand}$.

The exchange of oxygen and carbon dioxide with the lungs Lu of the patient P during the breathing and ventilation takes place only in the alveolar lung space. However, the upper airway and middle airway of the patient P, especially the trachea thereof, as well as an optional tube, hoses and/or other fluid-carrying units, which connect the patient P to the ventilator 1, as well as optionally measuring chambers, additionally belong to the fluid connection between the patient-side connection of the ventilator 1 and the lungs Lu. Breathing air or the other gas mixture flows through these areas or units/chambers during each ventilation stroke, but do not contribute to the exchange of oxygen or carbon dioxide and are hence designated as dead space. This dead space is composed of a patient-side dead space and a device-side dead space. The entire dead space volume $V_D$ is the sum of the volume $V_{D,Pat}$ of the patient-side dead space and the volume $V_{D,Ger}$ of the device-side dead space.

A marginal condition results from this dead space volume $V_D$ for the calculation of the mandatory ventilation frequency set point $f_{set,mand}$. The ventilation frequency $f_{ist}$ has namely to be low so that enough breathing air flows through the dead space and reaches the alveolar lung volume $V_A$.

During a ventilation stroke, the ventilator 1 feeds breathing air or another gas mixture containing oxygen into the fluid connection. The patient P takes in the gas mixture during a breath. The volume of the fed or of the taken-in gas mixture is designated as the tidal volume $Vol_{Tid,ist}$. Ideally, the lungs Lu are increased by this tidal volume $Vol_{Tid,ist}$ during each ventilation stroke. In one embodiment, it is required that the tidal volume $Vol_{Tid,ist}$ shall be at least twice as large as the dead space volume $V_D$. The marginal condition results from this and from the relationship $$f_{set,mand} \leq V'_{A,req}/V_D. \quad (3)$$

In an embodiment of the step of determining the patient-side dead space volume $V_{D,Pat}$, it is detected automatically when the patient P exhales. During exhalation, air flows out of the upper airway and middle airway of the patient P out of the body and, in addition, air flows out of the lungs Lu into the upper airway and middle airway and then outwards. A volume flow sensor, for example, the sensor 2 or the sensor 15, measures the respective volume flow Vol' at a point in the fluid connection at a plurality of scanning times. This measured volume flow Vol' correlates with the volume flow that flows into the body of the patient P and out of this patient. The CO2 content in the fluid connection is measured by means of a CO2 sensor. Only the alveolar lung space, but not the upper airway and middle airway, can feed CO2 into the air. As soon as this content is above a predefined threshold, the fluid connection contains gas exhaled out of the lungs Lu. In the period of time between the beginning of an exhalation process and the time, at which a relevant CO2 component is contained in the exhaled gas, gas flows out of the upper airway and middle airway from the patient P and into the fluid connection. The values for the volume flow, which are measured in the period of time up to the detection of CO2, yield, after integration, a value indicative of the dead space in the upper airway and middle airway of the patient P. The patient-side dead space volume $V_{D,Pat}$ can be determined, for example, by means of Bohr's formula.

As a rule, the volume $V_{D,Ger}$ of the device-side dead space in the fluid connection outside the body of the patient P is known with sufficient accuracy due to the construction of the ventilator 1 and the hoses. If the volume flow is measured close to the mouth of the patient P, the volume $V_{D,Ger}$ of the device-side dead space may be disregarded.

In another embodiment no CO2 sensor is needed. Rather, an ideal body weight $Gew_{id}$ of the patient P is determined, and the volume $V_{D,Pat}$ of the patient-side dead space in the upper airway and middle airway of the patient P is estimated according to the formula $$V_{D,Pat}=y*Gew_{id}. \quad (4)$$

Herein, y is an empirically determined factor.

An additional marginal condition results from the requirement that the actual ventilation frequency $f_{ist}$ has to be small enough to also still sufficiently expand less elastic lungs Lu, i.e., lungs with a high lung time constant $\tau$. In other words: In case of a ventilation frequency $f_{ist}$ that is too high, the pressure of the ventilation is not sufficient to sufficiently expand the lungs Lu. The lungs Lu cannot then take in enough oxygen and discharge enough CO2. This additional marginal condition depends on the lungs Lu of the patient.

The lung time constant $\tau$ varies from patient to patient and may also change in a patient over time. The lung time constant c is measured at the patient P to meet the just mentioned additional marginal condition. In a simplifying manner, the lungs can be considered to be a linear pneumatic system, wherein a pressure that is present in the lungs Lu overcomes pneumatic resistance and brings about an expansion of the elastic lungs Lu. Under this simplifying assumption, $$Vol_{Lu}(t) = Vol_{Lu,max} * \left[1 - e^{-\frac{T_i}{RC}}\right] \quad (5)$$

applies during the inhalation. Herein, R is the lung resistance (resistance) and C is the compliance. $Vol_{Lu}(t)$ is the volume of the lungs at the time t, $Vol_{Lu,max}$ is the maximum lung volume. Stated in a simplified manner, $$R=\Delta P/Vol' \quad (6)$$

applies to the lung resistance R, wherein $\Delta P$ is the difference between the maximum pressure and the minimum pressure over the course of a ventilation stroke and Vol' is the change of volume in the lungs Lu because of this pressure difference. The compliance C is the reciprocal of the elasticity E (elastance), wherein $$C=Vol/\Delta P \quad (7)$$

applies. The lung time constant $\tau$ is the product of the lung resistance R and the compliance C, i.e., $$\tau=R*C. \quad (8)$$

The lung time constant $\tau$ is a parameter, which describes in an idealized manner the response of the lungs, which are modelled as a passive pneumatic system, to a step function. In case of an intrinsic breathing activity of the patient P the step function results from an abrupt increase or even reduction of the pressure $P_{mus}$ generated by the diaphragm Zw; it results from an abrupt increase or reduction of the airway pressure $P_{aw}$ in case of a mechanical ventilation. As a response to the step function, the volume rises or falls exponentially, cf. the model equation (5) and the specification (8). When the lung time constant $\tau$ has elapsed since the step function, two-thirds, more precisely 63%, of the entire inspiratory tidal volume into the lungs Lu are then used. The lung time constant $\tau$ is stated, for example, in [msec] or in [sec].

At least one already mentioned volume flow sensor 2, 15 as well as at least one of the pressure sensors 2, 3, 7 that measure the volume flow Vol' or the airway pressure $P_{aw}$ in the fluid connection as well as optionally the esophageal pressure $P_{es}$ are used to determine the lung time constant $\tau$ of the patient P. The time course of the volume of the lungs Lu can be deduced from the volume flow Vol'. A typical value for the lung time constant $\tau$ of a COPD patient (patient with smoker's lung) is 450 msec. The lung time constant $\tau$ is, as a rule, markedly shorter in other patients.

The marginal condition is derived from the lung time constant $\tau$ preferably as follows: A factor x is predefined and does not depend on the lungs Lu of the patient P. The factor x is preferably between 4 and 12 and is, for example, 5.5 or 8. The resulting marginal condition is $$f_{set,mand}=1/(x*\tau). \quad (9)$$

An upper threshold $f_{set,mand,max}$ for the mandatory ventilation frequency set point $f_{set,mand}$, namely $$f_{set,mand,max}=\min \{V'_{A,req}/V_D, 1/(x*\tau)\} \quad (10)$$

results from the marginal conditions (3) and (9). It is possible to use a "safety margin," i.e., $$f_{set,mand,max}=\min \{(1-\lambda_1)*V'_{A,req}/V_D, 1-\lambda_2/(x*\tau)\} \quad (11)$$

with predefined values $\lambda_1$, $\lambda_2$.

Herein, $0<\lambda_1$, $\lambda_2<1$, preferably $\lambda_1$, $\lambda_2=0.2$.

$f_{set,mand}=f_{set,mand,max}$ must apply.

The specification $f_{set,mand}=f_{set,mand,max}$ would in many cases lead to an unnecessarily high ventilation frequency, especially to a ventilation frequency, which burdens the lungs Lu more intensely than necessary. Therefore, an ideal mandatory ventilation frequency set point $f_{set,mand,id}$ is calculated, which may be smaller, but not greater, than the upper threshold $f_{set,mand,max}$. The mandatory frequency set point $f_{set,mand}$ is specified according to the rule $$f_{set,mand}=\min \{f_{set,mand,id}, f_{set,mand,max}\}. \quad (12)$$

How the ideal mandatory ventilation frequency set point $f_{set,mand,id}$ is calculated is described below.

A ventilation stroke brings about an inhalation process. The inhalation process $T_i$ during mandatory ventilation has the same duration as the causative ventilation stroke. An expected or desired ratio of the duration $T_i$ of the inhalation compared to the duration $T_e$ of the exhalation during an individual ventilation process is predefined, i.e., the I:E ratio. Typical values are between 3:5 and 4:5. It is possible that this ratio depends on the lung time constant c of the patient P. From this results a predefined factor D1, which is the required time portion of the inhalation in an entire breathing cycle (breathing process), i.e., $$D1=T_i/(T_i+T_e) \quad (13)$$

This factor D1 acts as the required inhalation portion. It is also possible to directly predefine the $T_i/T_e$ quotient, i.e., the I:E ratio, as the inhalation portion. It is also possible to predefine a required average duration of an inhalation process or an exhalation process. A required inhalation portion D1 results from this duration of the inhalation process or exhalation process as well as from the ventilation frequency set point $f_{set}$.

The mandatory ventilation of the patient P performs mechanical work, which is split into resistive (viscose) work $W_R$ and elastic work $W_C$. The resistive work $W_R$ overcomes the lung resistance R. The elastic work $W_C$ expands the lungs Lu and acts against the elasticity and thus against the compliance C of the lungs Lu. Both the resistive work $W_R$ and the elastic work $W_C$ depend on the actual ventilation frequency $f_{ist}$.

As was already explained, the lungs Lu are modeled in a simplified manner as a linear pneumatic system. This system corresponds to an electrical RC element, i.e., to a series connection of an electrical resistor R and of an electrical capacitor C. For the subsequent deduction, it is assumed in a simplifying manner that the respective new pressure is immediately present during a ventilation stroke. In other words: A ventilation stroke is treated as a step function at the pneumatic system of the lungs. These simplifying assumptions lead to the following lung mechanical equations for the resistance power $W'_R$ as well as for the resistive power $W'_C$:

$$W'_R = \frac{f_{ist}}{2C}\left(\frac{\frac{V'_{A,ist}}{f_{ist}} + V_D}{1 - e^{-\frac{T_i}{RC}}}\right)^2 \left(1 - e^{-2\frac{T_i}{RC}}\right) = \frac{f_{ist}}{2C}\left(\frac{V'_{A,ist}}{f_{ist}} + V_D\right)^2 \coth\left(\frac{T_i}{2RC}\right) \quad (14)$$

$$W'_C = \frac{f_{ist}}{2C}\left(\frac{V'_{A,ist}}{f_{ist}} + V_D\right)^2 \quad (15)$$

The two lung mechanical equations (14) and (15) together form two components of a predefined lung model. They describe the resistive power $W'_R$ and the elastic power $W'_C$, respectively, which the ventilator 1 implements in case of mandatory ventilation during an inhalation process at the lungs Lu. They apply with sufficient accuracy to each value of the parameters C, R and $f_{ist}$ to be taken into consideration. According to this lung model (14) and (15), the resistive power $W'_R$ is, in any case, greater than the elastic power $W'_C$, regardless of how high the lung resistance R and the lung compliance C are and regardless of what actual ventilation frequency $f_{ist}$ is used during the mandatory ventilation.

Figure 2:
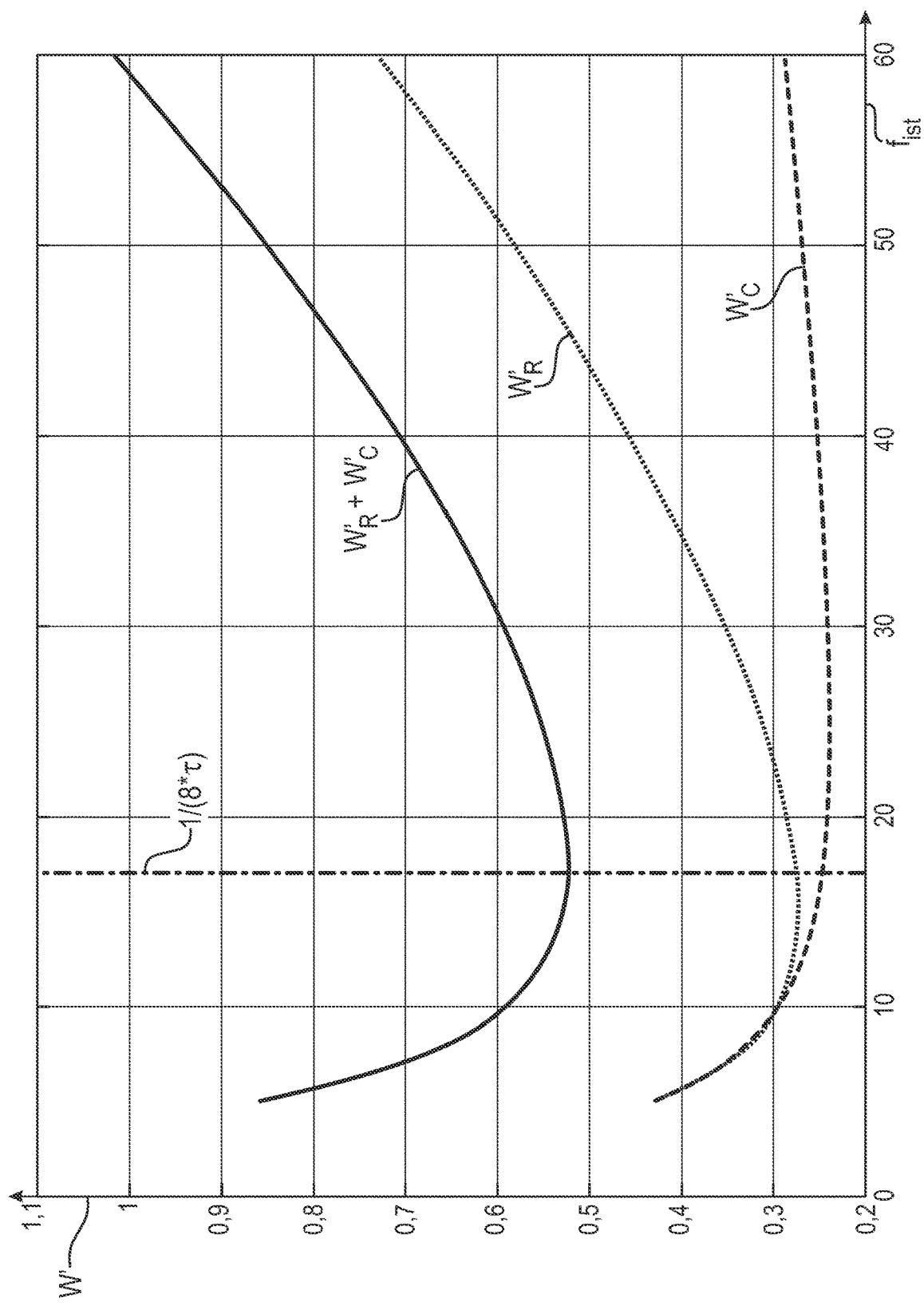
FIG. 2 is a graph showing in an exemplary manner the resistive power and the elastic power as a function of the actual ventilation frequency.

FIG. 2 shows in an exemplary manner the resistive power $W'_R$, the elastic power $W'_C$ as well as the overall mechanical power, i.e., the sum $W'_R + W'_C$, as a function of the actual ventilation frequency $f_{ist}$. The ventilation frequency $f_{ist}$ in [1/min] is plotted on the x axis, and the power in [Nm/sec] is plotted on the y axis. In addition, the upper threshold for the ventilation frequency $f_{ist}$, which results from the marginal condition (9) with the value x=8, is plotted as a vertical line in FIG. 2.

Figure 3:
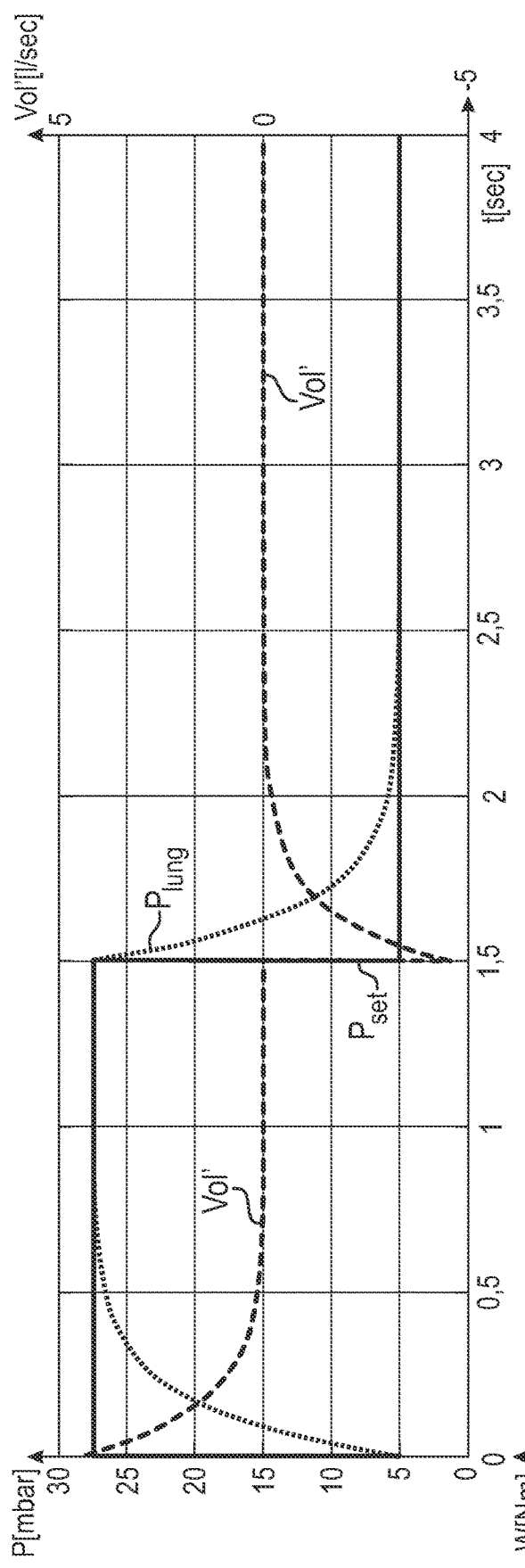
FIG. 3 is a graph showing in an exemplary manner the respective time curves (each time course) of pressure, volume flow, resistive work and elastic work in case of a relatively low lung resistance.
Figure 3:
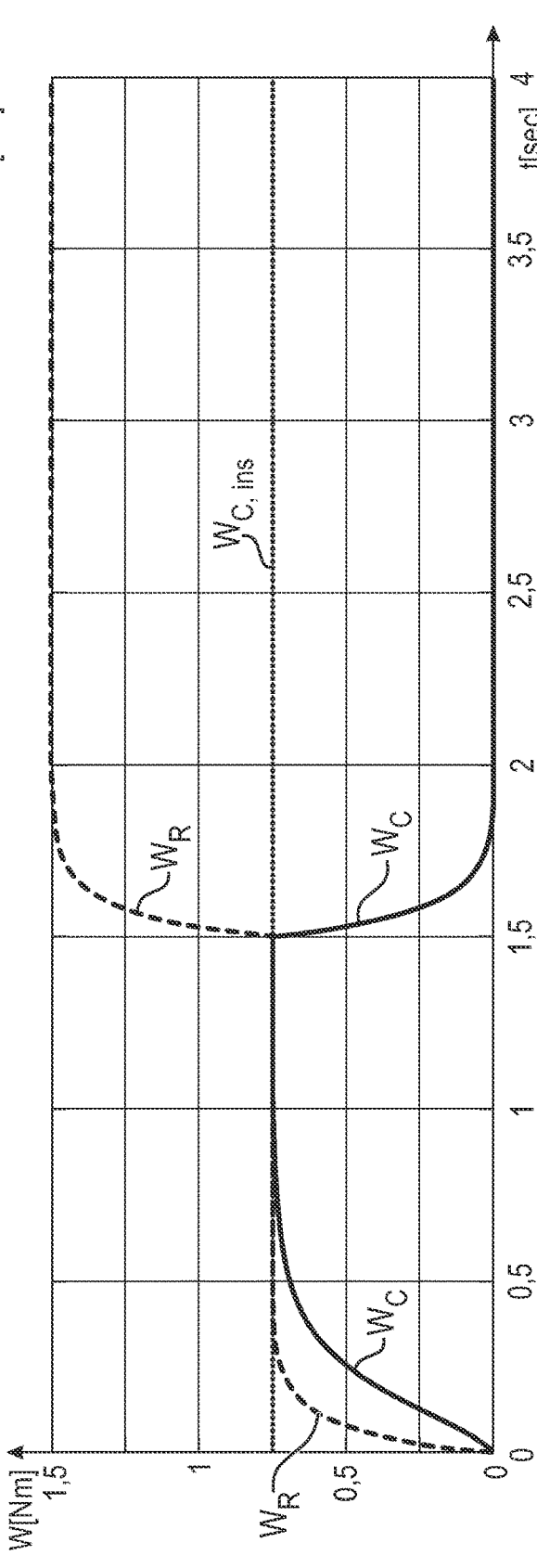
Figure 4:
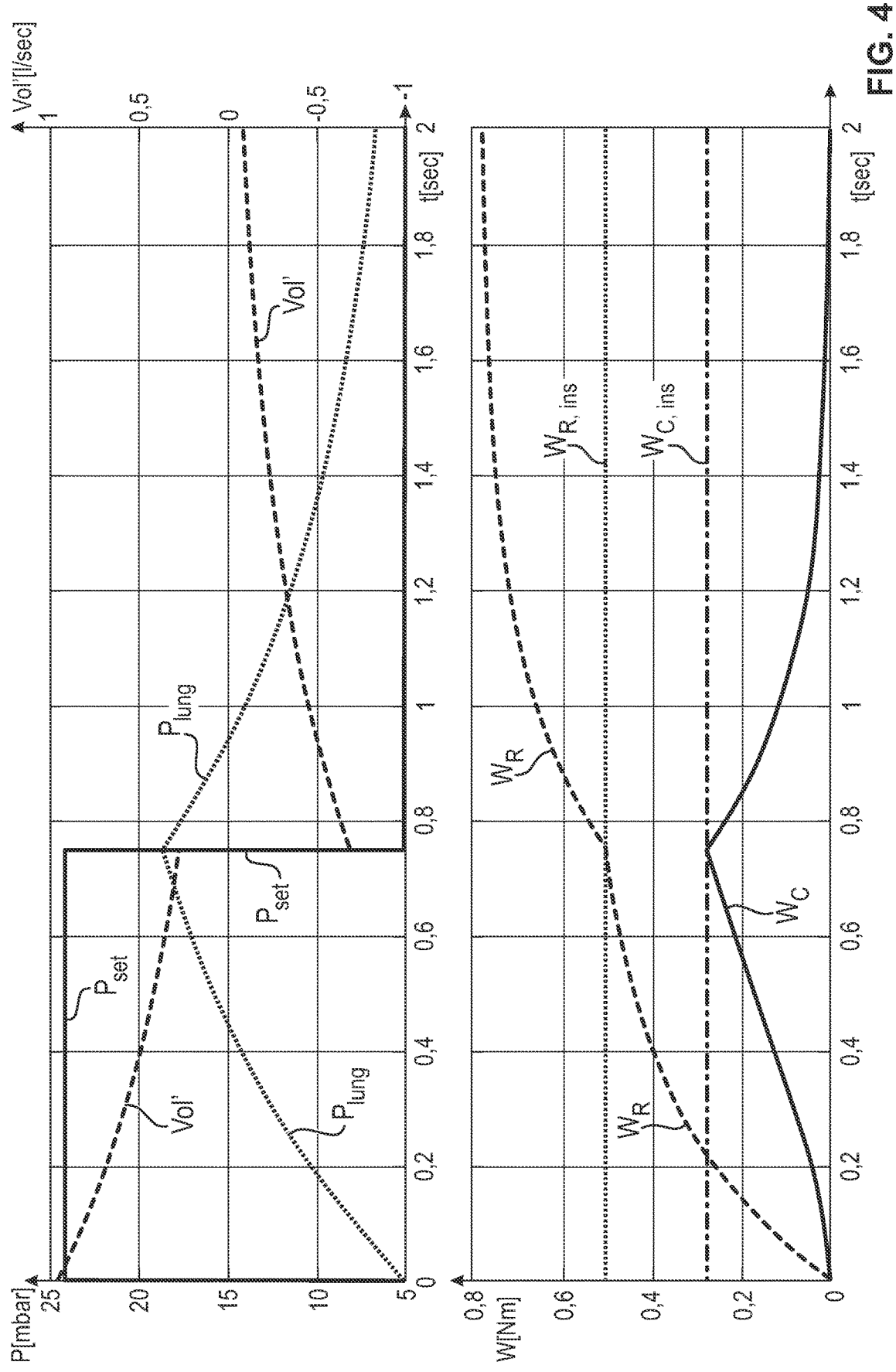
FIG. 4 is a graph showing in an exemplary manner the respective time course of pressure, volume flow, resistive work and elastic work in case of a relatively high lung resistance and in case of a relatively high ventilation frequency.

FIG. 3 and FIG. 4 show in an exemplary manner the time course of the pressure P (top) and the time course of the work W performed (bottom) during a ventilation stroke. The time t in seconds is plotted on the x axis, the pressure P in [mbar] as well as the volume flow Vol' in [L/sec](top) and the work W in [Nm](bottom) are plotted on the y axis. Each time course is determined by means of the two lung mechanical equations (14) and (15). C=30 mL/mbar in this example. The alveolar minute volume $V'_{A,ist}$ achieved is $V'_{A,ist}$=7.9 L/min. R =5 mbar/(L*sec) in FIG. 3, and R=20 mbar/(L*sec) in FIG. 4. The actual ventilation frequency is in the example of FIG. 3 $f_{ist}$ 15/min, in the example of FIG. 4 $f_{ist}$=30/min.

In the views of each time course
$P_{set}$ denotes the time course of the pressure to be generated by the ventilator 1, wherein the time course $P_{set}$ is a command variable for a lower-level control of the actually achieved pressure, and the actual pressure (controlled variable) is preferably measured as the achieved airway pressure $P_{aw}$,
$P_{lung}$ denotes the time course of the resulting pressure in the lungs Lu,
Vol' denotes the volume flow in the fluid connection to the patient P and optionally from the patient P, wherein a positive value denotes a volume flow from the ventilator 1 to the patient P and a negative value denotes a volume flow from the patient P to the ventilator 1,
$W_R$ denotes the resistive work performed up to the pint in time,
$W_C$ denotes the elastic work performed up to the point in time,
$W_{R,ins}$ denotes the resistive work performed at the end of an inhalation process, and
$W_{C,ins}$ denotes the elastic work performed at the end of an inhalation process.
$W_{R,ins}$=0.76 Nm and $W_{C,ins}$=0.76 Nm in the example of FIG. 3 and $W_{R,ins}$=0.50 Nm and
$W_{C,ins}$=0.28 Nm in the example of FIG. 4.

In the two examples that are shown in FIG. 3 and FIG. 4 the set pressure $P_{set}$ during a ventilation stroke increases immediately to the maximum value. Therefore, FIG. 3 and FIG. 4 show the response of the pneumatic system of the lungs to a step function by the ventilator 1. In reality, the actual pressure $P_{aw}$ achieved due to the lower-level control cannot immediately increase to the full value. In addition, it must be ruled out or at least the risk must be reduced that the lungs Lu of the patient P are damaged by an increase in pressure that is too rapid. Therefore, the desired time course $P_{set}$ of the pressure is predefined such that it increases at the beginning of a ventilation stroke until it reaches the maximum value. This period of time between the beginning of the ventilation stroke and reaching the maximum value for the pressure $P_{aw}$ is designated as the actual ramp time $t_{R,ist}$. The desired time course $P_{set}$ of the pressure comprises an increase in pressure in a predefined set ramp time $t_{R,ist}$ and subsequently a maximum set pressure. Since a set ramp time $t_{R,set}$ is predefined, the resistive work $W_R$ is reduced compared with an abrupt increase in the set pressure $P_{set}$, while the elastic work $W_C$ remains unchanged. One reason for this: The maximum volume flows are reduced.

In a preferred embodiment, the set ramp time $t_{R,set}$ is specified as a function of the determined lung time constant $\tau$ of the patient P, for example, according to the calculation rule $$t_{R,set} = \gamma * \tau. \quad (16)$$

In this case, the factor $\gamma$ is predefined and is stored in the memory 11 and is, for example, $\gamma$=0.5.

Figure 5:
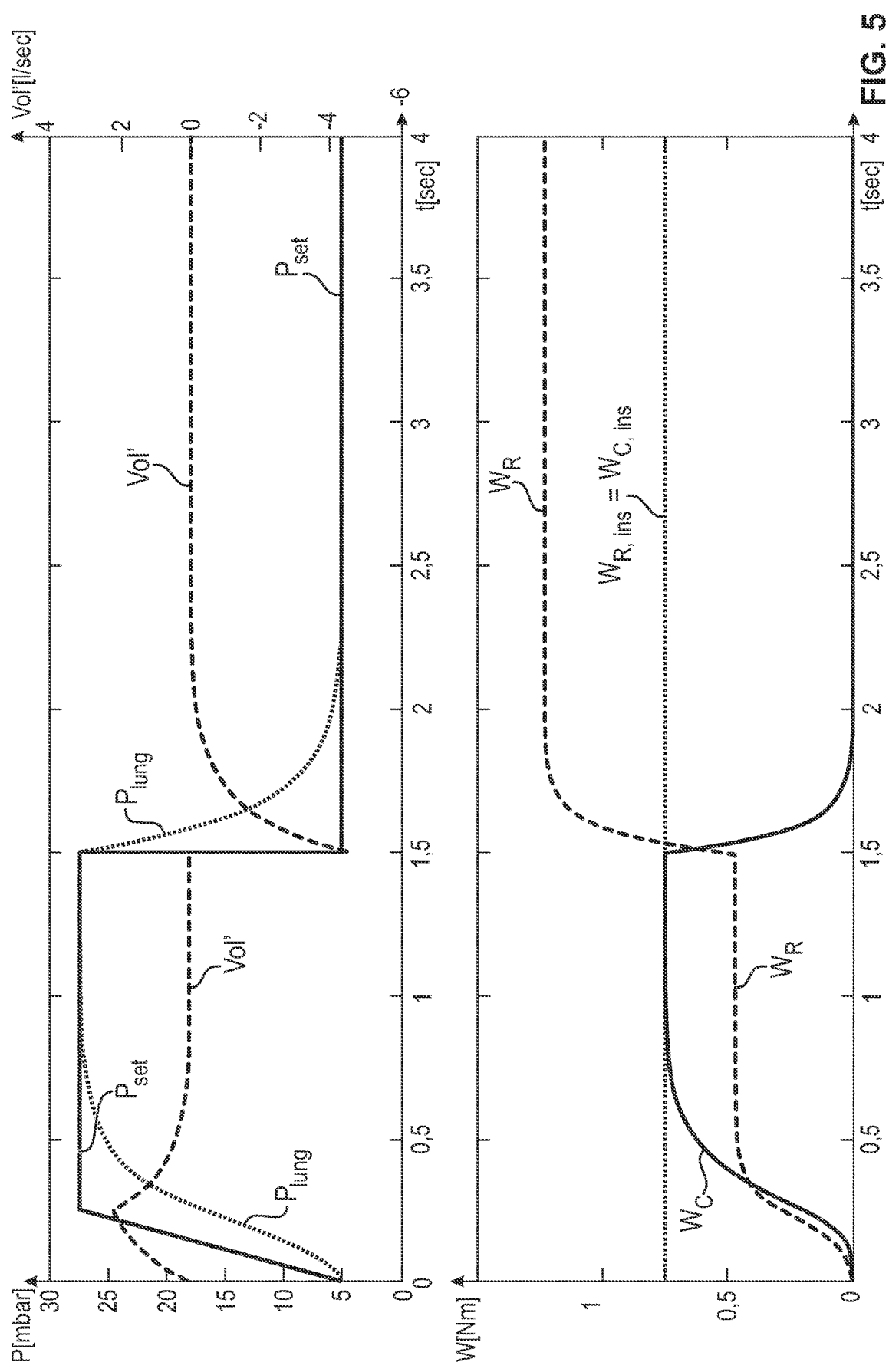
FIG. 5 is a graph showing in an exemplary manner the respective time course of pressure, volume flow, resistive work and elastic work in case of a relatively low lung resistance, wherein the ramp time is taken into consideration at the beginning of a ventilation stroke.

FIG. 5 shows the time curves which are also shown in FIG. 3 and FIG. 4, wherein a controlled increase in pressure is carried out in the example of FIG. 5. In the example of FIG. 5, the lung compliance C=30 mL/mbar, the lung resistance R=5 mbar/(L*sec), the ventilation frequency $f_{ist}$=15/min and the ramp time $t_{R,ist}$=0.25 sec. A minute volume of $V'_{A,ist}$=7.9 L/min is achieved. The resistive work $W_R$ is lower when the ramp time $t_{R,ist}$ is taken into consideration compared with a ventilation without a ramp time (step response, i.e., $t_{R,ist}$=0). The elastic work $W_C$ remains unchanged.

The resistive work performed at the end of an inhalation process is $W_{R,ins}$=0.47 Nm, and the elastic work performed at the end of an inhalation process is $W_{C,ins}$=0.76 Nm. The resistive work that is performed at the end of an exhalation process is $W_{R,exp}$=0.76 Nm, the elastic work performed at the end of an exhalation process is $W_{C,exp}$=−0.76 Nm.

Both the resistive power $W'_R$ and elastic power $W'_C$ depend on the actual ventilation frequency $f_{ist}$. The resistive power $W'_R$ is always greater than the elastic power $W'_C$. The ideal mandatory frequency set point $f_{set,mand,id}$ is specified as a function of the effect of the actual ventilation frequency $f_{ist}$ on the resistive power $W'_R$ and on the elastic power $W'_C$.

The ventilation strokes during mandatory ventilation bring about each an inhalation process of the patient P. From this follows:

$$f_{ist} * T_i = \frac{T_i}{T_e + T_i} = D1 \quad (17)$$

For the following deduction, it is assumed that the actual frequency $f_{ist}$ of the mandatory ventilation is equal to the ideal mandatory ventilation frequency set point $f_{set,mand,id}$ to be calculated, i.e., the following applies:

$$f_{ist} = f_{set,mand,id} \quad (18)$$

The relationship (17) shows how under the assumption (18) the sought ideal ventilation frequency $f_{set,mand,id}$, the duration $T_i$ of a ventilation stroke and the time-related inhalation portion D1 are connected to one another.

A defined actual ventilation frequency $f_{ist}$ and a defined duration $T_i$ of the ventilation strokes lead according to the lung mechanical model equations (14) and (15) to a defined resistive power $W'_R$ and to a defined elastic power $W'_C$.

In one embodiment the sought ideal mandatory ventilation frequency set point $f_{set,mand,id}$ is calculated such that a function, which depends on the two mechanical powers $W'_R$ and $W'_C$, is minimized. This function is, for example, the sum of the two powers, i.e., $W'_R + W'_C$, or the quotient $W'_R/W'_C$ of the two powers.

By contrast, the ideal mandatory ventilation frequency set point $f_{set,mand,id}$ is calculated in a preferred embodiment of the exemplary embodiment such that the elastic power $W'_C$ is approximately equal to the resistive power $W'_R$. In many cases, this specification leads to a comparatively low mechanical stress of the lungs Lu of the patient P. Stated more precisely: A factor $\alpha$ is predefined, wherein a is preferably between 0 and 0.2 and is especially preferably equal to 0.1. $1+\alpha$ then acts as a capacity (power) factor. The marginal condition in case of the specification of the ideal mandatory ventilation frequency set point $f_{set,mand,id}$ is $$\frac{W'_R}{W'_C} = 1 + \alpha \quad (19)$$

From the equations (15) und (19) follows $$\frac{W'_R}{W'_C} = \coth\left(\frac{T_i}{2RC}\right) \quad (20)$$

If the equations (20) and (17) are each solved for $T_i$ under this assumption, then the following calculation rule results for the ideal mandatory ventilation frequency set point $f_{set,mand,id}$:

$$f_{set,mand,id} = \frac{D1}{2 * RC * \text{arccoth}(1+\alpha)}. \quad (21)$$

Herein $$\text{arccoth}(1+\alpha) = \frac{1}{2}\ln\frac{2+\alpha}{\alpha}. \quad (22)$$

applies. In addition, the marginal conditions (3) and (9) shown above are to be taken into account, i.e., the upper threshold $f_{set,mand,max}$. The mandatory ventilation frequency set point $f_{set,mand}$ is specified according to the calculation rule (17) for the ideal mandatory ventilation frequency set point $f_{set,mand,id}$, unless an upper threshold $f_{set,mand,max}$ leads to a lower value, cf. the specification rule (12). The following calculation rule results from this for the mandatory ventilation frequency set point $f_{set,mand}$:

$$f_{set,mand} = \min\left\{\frac{D1}{2*RC*\text{arccoth}(1+\alpha)}, \frac{V'_{A,req}}{V_D}, \frac{1}{x*\tau}\right\} \quad (23)$$

The lung time constant $\tau$ is measured at the patient P. For this purpose, the signal processing unit 10 preferably analyzes measured values from the sensors 3 and 15 and thereby determines the airway pressure $P_{aw}$ and the volume flow Vol'. The signal processing unit 10 deduces an estimate for the product R*C from these signals and uses this estimate as the lung time constant $\tau$ of the patient P. In a simplifying manner, an ideal step increase of the pressure $P_{aw}$ can be assumed in case of the determination of the lung time constant $\tau$, and the lung time constant $\tau$ can then be deduced solely from the measured volume flow Vol'.

The action of specifying the mandatory ventilation frequency set point $f_{set,mand}$ according to the calculation rule (23) leads to a simple and robust specification of a set point $f_{set,mand}$ for the ventilation frequency $f_{ist}$ under mandatory ventilation. In many cases a lower ventilation frequency set point $f_{set,mand}$ is calculated than in other processes, so that the action according to the present invention leads to a lower stress of the mechanically ventilated lungs, especially in a patient P with a relatively low lung time constant c.

An advantage of the just described embodiment is that the lung resistance R and lung compliance C do not have to be measured separately from one another. This is especially when the patient P is breathing spontaneously, prone to relatively great uncertainty. It is sufficient to measure the lung time constant $\tau$i, i.e., the product R*C. A sufficiently reliable value for the lung time constant c is, as a rule, obtained after a few breaths, which the intrinsic respiratory muscles of the patient P carries out, or a few ventilation strokes of the ventilator 1.

In contrast to other processes, which automatically specify a ventilation frequency, the embodiment just described does not require that an optimization be carried out at the run time. In particular, it is not necessary to determine the ventilation frequency set point at the run time such that a function, which is dependent on the ventilation frequency $f_{set}$, which belongs to a lung mechanical model, is minimized. In other processes, this function describes, for example, the work during a ventilation stroke or the power that is applied during the ventilation stroke. If an optimization were needed at the run time, then a relatively high computing capacity and/or a relative long computing time would be needed. In practice, an optimization is frequently carried out by means of an iterative process, which is completed when an interruption criterion is met. In some cases, the value found may be relatively far away from an optimum.

The just described action also does not necessarily require that during the mechanical ventilation a so-called maneuver is carried out, in which an operating parameter of the ventilator 1, for example, a required time course of the pressure or of the volume flow is set for a short period of time specifically to a different value in order to measure a vital parameter of the patient P. In particular, no occlusion is necessary, in which the mechanical ventilation is set for a short period of time and optionally also the intrinsic breathing activity of the patient P is stopped for this short period of time in order to measure the pressure, which is variable over time and which is caused by the intrinsic breathing activity of the patient P. Such a maneuver frequently stresses the patient P.

In many cases the just described action according to the present invention leads to the mandatory ventilation being carried out with a ventilation frequency $f_{ist}$, which is not higher than necessary, in order to achieve the desired alveolar minute volume $V'_{A,req}$. This action reduces for this reason in many cases the mechanical stress of the lungs Lu of the patient P and therefore reduces the risk that the lungs Lu of the patient P are damaged mechanically.

The desired alveolar minute volume $V'_{A,req}$ is predefined for the mechanical ventilation. Procedures for doing this are used as are described, for example, in J. Fernández, D. Miguelena, H. Mulett, J. Godoy, and F. Martinón-Torres, "Adaptive support ventilation: State of the art review," *Indian J. Crit. Care Med.*, vol. 17, No. 1, p. 16, 2013.

Also, at the beginning of the mechanical ventilation, the entire dead space volume $V_D$ is determined, preferably using one of the two methods described above. The patient-side dead space volume $V_{D,Pat}$ is preferably measured repeatedly during the entire mechanical ventilation, and, especially a change in the patient-side dead space volume $V_{D,Pat}$ is detected and taken into consideration as a result. The factors α and x are preferably permanently predefined once and are then stored in the ventilator 1. In this embodiment, a constant const is determined and stored at the beginning of the mechanical ventilation of the patient P or even beforehand, namely in the exemplary embodiment according to the calculation rule $$const = \min\left\{\frac{D1}{2*\text{arccoth}(1+\alpha)}, \frac{1}{x}\right\} \quad (24)$$

This leads to the following calculation rule:

$$f_{set,mand} = \min\left\{\frac{V'_{A,req}}{V_D}, \frac{const}{\tau}\right\} \quad (25)$$

In the embodiment described up to now, a value for the factor α is predefined. It is also possible to predefine n values $\alpha_1, \ldots, \alpha_n$ for the factor α. The just described calculation is carried out for each predefined factor $\alpha_1, \ldots, \alpha_n$. This yields n values $f_{set,mand}(\alpha_1), \ldots, f_{set,mand}(\alpha_n)$. A value, which is calculated by a suitable averaging or formation of the median or other aggregation from these n values, for example, the smallest value, is used as the mandatory ventilation frequency set point $f_{set,mand}$.

The action described above shows a way to automatically deduce a ventilation frequency set point $f_{set,mand}$ for a mandatory mechanical ventilation of the patient P. A desired alveolar minute volume $V'_{A,req}$ or even a proximal minute volume is predefined for this. This ventilation frequency set point $f_{set,mand}$ is then used for the above-described lower-level control, when the patient P is fully anesthetized and is therefore not carrying out intrinsic breathing activity.

As already mentioned, a desired alveolar minute volume $V'_{A,req}$ is predefined for the process. If the patient P is fully anesthetized, then this minute volume $V'_{A,req}$ is generated exclusively by the mechanical ventilation (mandatory ventilation). This mandatory ventilation is carried out with the ventilation frequency set point $f_{set,mand}$, which is specified as just described.

However, it is also possible that the patient P carries out an intrinsic breathing activity, is especially breathing spontaneously, and himself applies a component of the desired alveolar minute volume $V'_{A,req}$. If the alveolar minute volume, which the patient P applies by his intrinsic breathing activity, is designated by $V'_{A,spon}$, then $$SML = V'_{A,spon}/V'_{A,req} \quad (26)$$

applies. This factor SML is likewise determined and used.

A value indicative of the vacuum $P_{mus}$ which is generated by the activity of the diaphragm Zw and of the intercostal muscles of the patient P is measured in one embodiment. Both the airway pressure $P_{aw}$, which is present in the lungs Lu from outside, and the vacuum $P_{mus}$ acting from inside on the lungs Lu, are then known. The alveolar minute volume $V'_{A,spon}$, which is achieved exclusively by the intrinsic breathing activity of the patient P, is deduced from the two signals $P_{aw}$ and $P_{mus}$. Because the signal $P_{aw}$ is brought about by an overlapping of the intrinsic breathing activity with the mechanical ventilation, the signal $P_{mus}$ is brought about exclusively by the intrinsic breathing activity.

In one embodiment, in order to measure a value indicative of the vacuum $P_{mus}$, the esophageal pressure $P_{es}$ is measured. This embodiment presumes that the probe 3 is inserted into the esophagus Sp of the patient P and measures a value indicative for the esophageal pressure $P_{es}$. In another embodiment, signals from the measuring electrodes 5.1.1 through 5.1.2 are used to measure the electrical activity of the muscles of the breathing apparatus of the patient P approximately. This electrical activity brings about the intrinsic breathing activity of the patient P and does not depend on the mechanical ventilation.

In another embodiment, the fact is utilized that when the intrinsic breathing activity of the patient P is assisted by the processing device (ventilator) 1, spontaneous or stimulated breaths of the patient P are detected and each detected, sufficiently great spontaneous or stimulated breath triggers a ventilation stroke of the ventilator 1. The more the patient triggers ventilation strokes of the ventilator 1, the more intensive is his intrinsic breathing activity. How many ventilation strokes per time unit the intrinsic breathing activity of the patient P triggers is counted. This other embodiment does not necessarily require determining the alveolar minute volume $V'_{A,spon}$.

Figure 6:
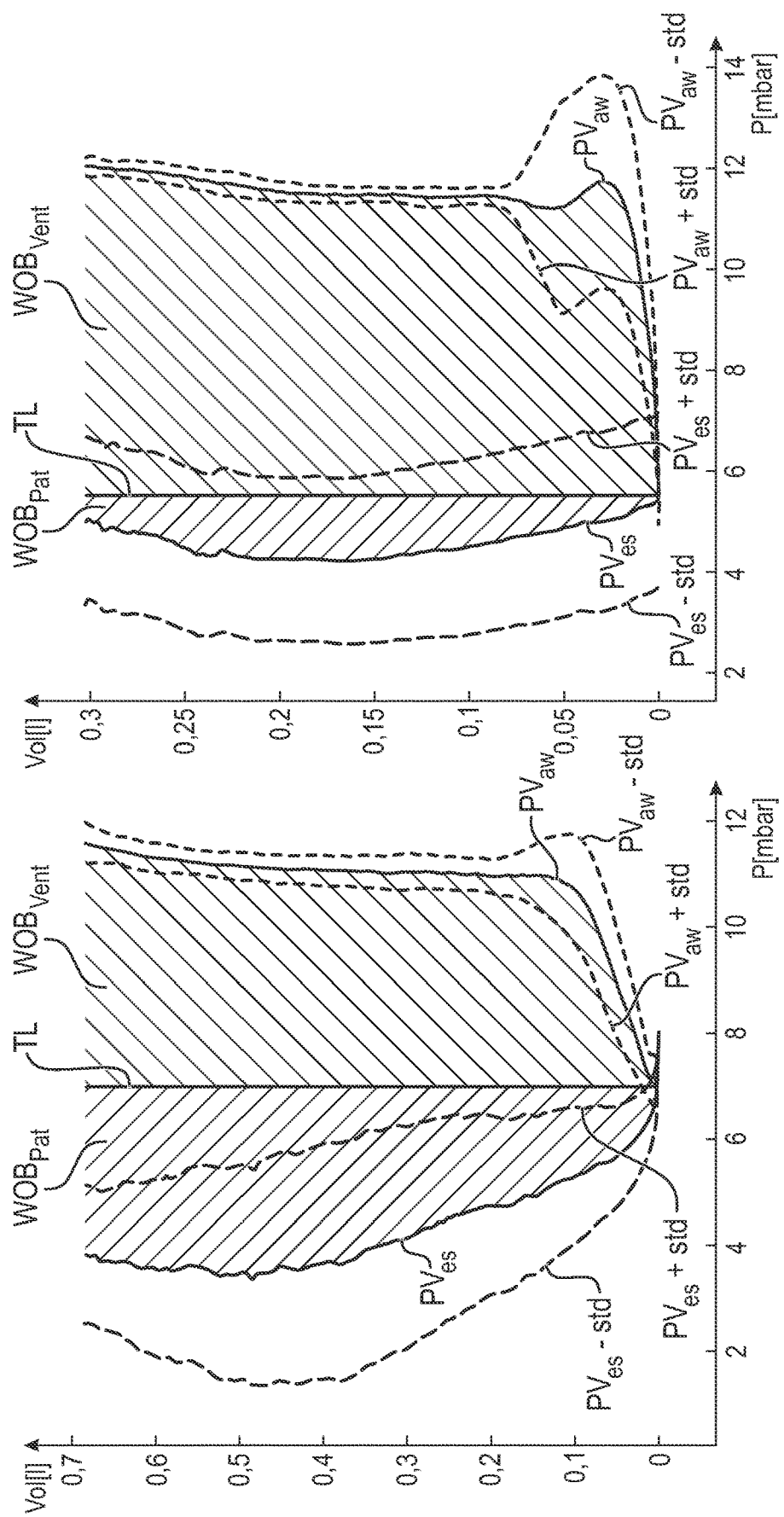
FIG. 6 is a graph showing how the value indicative of the intensity of the intrinsic breathing activity of the patient is determined as a function of the breathing work performed.
Figure 7:
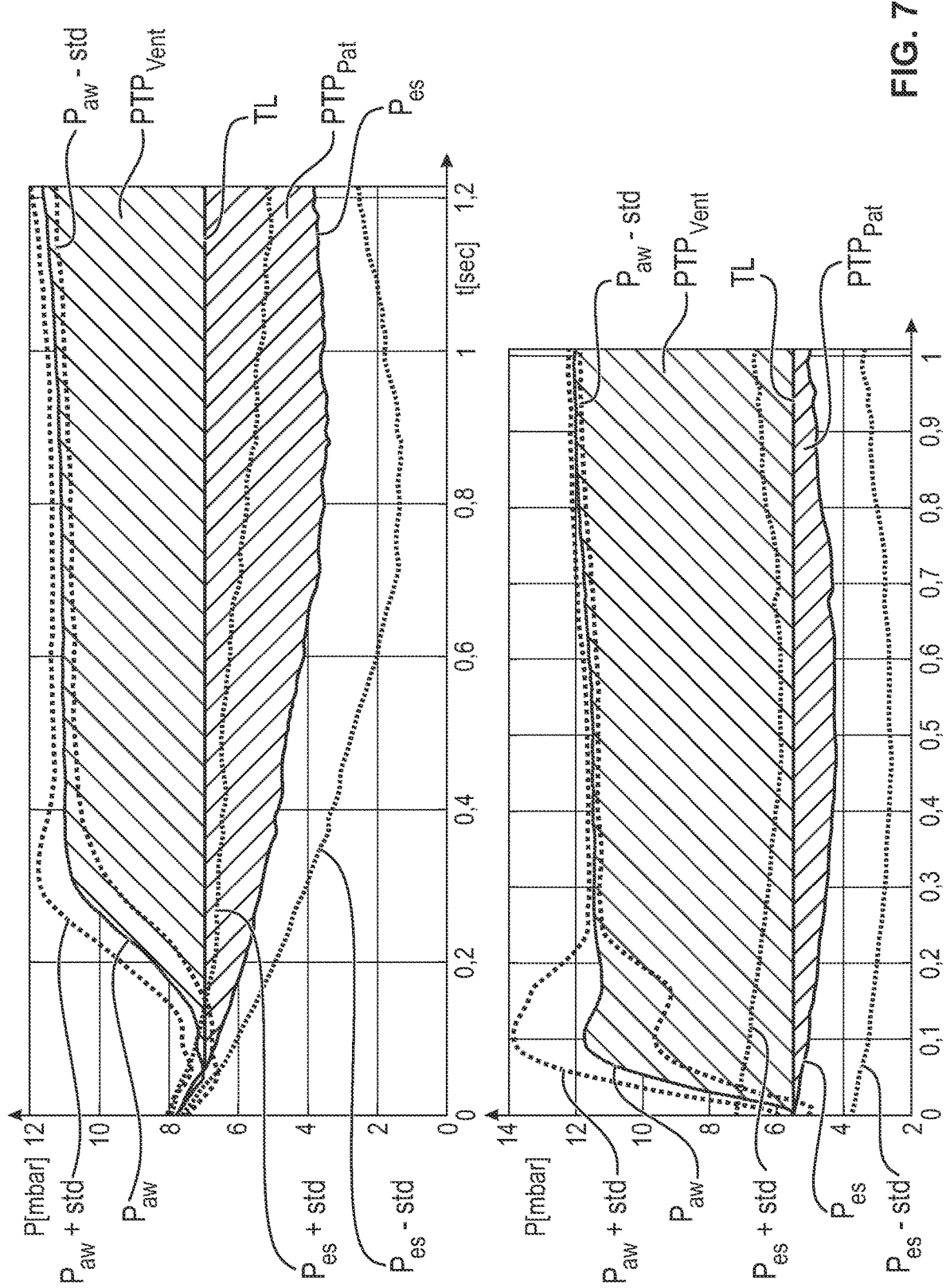
FIG. 7 is a graph showing how the value indicative of the intensity of the intrinsic breathing activity is determined as a function of the occurring pressure-time product.

FIG. 6 and FIG. 7 illustrate two embodiments with regard to how the value indicative of the intensity of the intrinsic breathing activity of the patient P is determined. At the beginning of each period of time taken into consideration, the patient P does not carry out any intrinsic breathing activity, and the ventilator 1 also does not carry out any ventilation stroke, so that at the start of the period of time the two pressures $P_{aw}$ and $P_{es}$ agree approximately. Subsequently, these two pressures differ from one another because of his intrinsic breathing activity and/or mechanical ventilation.

The work (work of breathing, WOB), which is applied during one breath for inhaling, is used in the embodiment according to FIG. 6. The pressure P in [mbar] is plotted on the x axis, while the volume Vol in [L] flowing into the lungs Lu and out of the lungs Lu is plotted on the y axis. The esophageal pressure $P_{es}$, which is measured by means of the probe 3, is used as a value indicative of the pressure generated by the diaphragm Zw of the patient P.

The curves shown in FIG. 6 are obtained by an overlap of a plurality of breaths, by the respective median, or the mean value as an alternative, being formed in the exemplary embodiment. The parameters shown are each interpreted as a normally distributed random variable. The standard deviation, i.e., a tolerance range around the median, is shown as measuring inaccuracy.

In FIG. 6, $PV_{es}$ denotes the pressure-volume curve, which the diaphragm Zw applies, i.e., the volume achieved as a function of the pressure $P_{mus}$, $PV_{aw}$ denotes the pressure-volume curve, which the ventilator 1 applies, measured with the sensor 2 at the mouth of the patient P and optionally with the sensor 15 at the ventilator 1, TL denotes a separation line, which runs through the intersection of $PV_{es}$ and $PV_{aw}$, $WOB_{Pat}$ denotes the work applied by the patient P by his intrinsic breathing activity during an inhaled breath, wherein the work is equal to the area between the pressure-volume curve $PV_{es}$ and the separation line TL, $WOB_{Vent}$ denotes the work applied by the mechanical ventilation by the ventilator 1 during an inhaled breath, wherein the work is equal to the area between the pressure-volume curve $PV_{aw}$ and the separation line TL, and std denotes the standard deviation around the median.

In one embodiment, the esophageal pressure $P_{es}$ is measured, namely by means of the probe 3 in the esophagus Sp of the patient P as a value indicative of the pressure $P_{mus}$, which the diaphragm Zw applies. In another embodiment, the course over time of the pressure $P_{aw}$ and the volume flow Vol' are measured at the mouth of the patient P, preferably by means of the sensor 2 and optionally by means of the sensor 15, and a value indicative of the pressure $P_{mus}$ is derived from these time curves by means of a lung model. An average of a plurality of inhaled breaths is preferably formed.

The entire work WOB applied during an inhaled breath is the sum of $WOB_{Pat}$ and $WOB_{Vent}$. The portion of the work applied by the patient P of the overall work WOB, i.e., $$SML = WOB_{Pat}/(WOB_{Pat} + WOB_{Vent}) \quad (27)$$

is calculated and used as a value indicative of the portion of the intrinsic breathing activity of the patient P. In the example of FIG. 6, the factor SML is about 41% in the example on the left-hand side and is only 13% in the example on the right-hand side.

In the just described embodiment, an averaged work is preferably calculated. Using this approach, the intrinsic breathing activity of the patient P is relatively easily detected quantitatively.

In the embodiment according to FIG. 7, the averaged pressure P is used during an inhaled breath. PTP means "pressure-time product." The time t in [sec] is plotted on the x axis, and the pressure in [mbar] for the two pressures $P_{aw}$ and $P_{es}$ is plotted on the y axis. The separation line TL runs through the intersection of the curves of $P_{aw}$ and $P_{es}$. The area $PTP_{Pat}$ between the time course of the pressure $P_{es}$ and the separation line TL is a value indicative of the average pressure $P_{mus}$, which the patient P applies through his intrinsic breathing activity, and correlates with the mechanical power of the intrinsic breathing activity of the patient P. The area $PTP_{Vent}$ between the time course of the pressure $P_{aw}$ and the separation line TL is a value indicative of the mean pressure $P_{aw}$ applied by the ventilator 1 and correlates with the mechanical power of the mechanical ventilation. The following quotient $$SML = PTP_{Pat}/(PTP_{Pat} + PTP_{Vent}). \quad (28)$$

is used as a value indicative of the portion of the intrinsic breathing activity of the patient P. The portion of the intrinsic breathing activity is markedly greater in the example shown at the top in FIG. 7 than in the example shown at the bottom.

At the start of the mechanical ventilation, the ventilator 1 is operated such that a desired time course of the airway pressure $P_{aw}$ or even of the volume flow Vol' is achieved during the mechanical ventilation. A desired time course is predefined and a lower-level regulation or control is carried out with the goal that the actual time course is equal to the desired time curve. The ventilator 1 carries out a series of ventilation strokes during the mechanical ventilation. Some of these ventilation strokes are triggered by the intrinsic breathing activity of the patient P, the rest are automatically triggered by the ventilator 1 in order to achieve the desired time course of the pressure or volume flow. In the case of a sufficiently intensive intrinsic breathing activity, it is also possible that each ventilation stroke of the ventilator 1 is triggered by a breath of the patient P.

The factor SML is calculated, e.g., according to one of the calculation rules (26), (27), (28) or according to $$SML = n_{spon}/n_{ges}. \quad (29)$$

Herein, $n_{spon}$ denotes the number of ventilation strokes, which are triggered within a period of time by the intrinsic breathing activity of the patient P, and $n_{ges}$ denotes the number of all the ventilation strokes of the ventilator 1 carried out in this period of time.

In addition, an ideal frequency $f_{spon}$ of the intrinsic breathing activity of the patient P is calculated. In this case, it is preferably assumed in a simplifying manner that the intrinsic breathing activity of the patient P has a sinusoidal time curve. If the patient P can take in the desired alveolar minute volume $V'_{A,req}$ exclusively by his intrinsic breathing activity, then he is breathing according to this simplification with the ideal frequency $$f_{spon} = \frac{\sqrt{1 + 4*\pi^2*\tau*\frac{V'_{A,req}}{V_D}} - 1}{2*\pi^2*\tau} \quad (30)$$

This ideal frequency $f_{spon}$ requires the lowest power $W'_R + W'_C$ to achieve the desired alveolar minute volume $V'_{A,req}$ by the intrinsic breathing activity. In other words: Any other frequency of the intrinsic breathing activity requires a higher power.

The entire dead space volume $V_D$, i.e., also the device-side dead space volume $V_{D,Ger}$ in addition to the patient-side dead space volume $V_{D,Pat}$, is taken into consideration in this calculation.

A similar calculation rule may be used such as is already specified in J. Mead: "Control of respiratory frequency," *J. Appl. Physiol.*, vol. 15, No. 3, pp. 325-326, 1960.

Other calculation rules are also possible. For example, an ideal frequency of the intrinsic breathing activity is determined, which, at a given desired alveolar minute volume $V'_{A,req}$, leads to a minimal amplitude of the generated pressure, which is variable over time.

The ventilation frequency set point $f_{set}$ of the ventilator 1 is specified as follows:

$$f_{set} = SML*f_{spon} + (1-SML)*f_{set,mand}. \quad (31)$$

Herein, $f_{spon}$ is the ideal frequency of the intrinsic breathing activity, which is calculated according to the calculation rule (30), for example, $f_{set,mand}$ is the ventilation frequency set point specified according to the present invention for the mandatory ventilation and SML is the factor, which is specified, for example, according to the calculation rule (29) or using the esophageal pressure $P_{es}$ according to the calculation rule (28) or according to (27) or (28).

The embodiment according to specification rule (31) avoids an abrupt transition between an assisted ventilation and a mandatory ventilation, when the intrinsic breathing activity of the patient P changes. Rather, a gradual transition is reached, wherein the stronger the intrinsic breathing activity of the patient P is, the weaker is the mandatory ventilation, and vice versa.

It is ensured due to a deviation that the ventilation frequency set point $f_{set}$ is at least as high as the ideal frequency $f_{spon}$ of the intrinsic breathing activity. The calculation rule according to the deviation is $$f_{set,mand} = \min\left\{\frac{V'_{A,req}}{V_D}, \frac{const}{\tau}\right\}, \text{falls } \frac{V'_{A,req}}{V_D} > f_{spon} \text{ und} \frac{const}{\tau} \quad (32)$$

$$f_{set,mand} = f_{spon} \text{ ansonsten}$$

This deviating calculation rule ensures that $f_{set,mand} \geq f_{spon}$ and hence also $f_{set} \geq f_{spon}$ applies. Also, in case of this deviating calculation rule, the ventilation frequency set point $f_{set}$ is specified according to the calculation rule (31).

An operating parameter which can be set at the ventilator 1 is the set tidal volume $Vol_{Tid,set}$, i.e., the volume, which shall be applied in the mouth of the patient P during a breathing cycle. This volume essentially corresponds to the volume, which shall be discharged from the ventilator 1 during a ventilation stroke. A lower-level regulation or control obtains the set tidal volume $Vol_{Tid,set}$ as a specification and actuates the ventilator 1 with the goal that the tidal volume $Vol_{Tid,ist}$ that is actually achieved by the ventilation strokes is equal to the calculated set tidal volume $Vol_{Tid,set}$.

During an inhalation process, the actually achieved tidal volume $Tid_{Vol,ist}$ is discharged into the fluid connection and is split up into the achieved alveolar lung volume $V_{A,ist}$ as well as the dead space in the hoses of the fluid connection as well as in the upper airway and middle airway of the patient P, wherein the overall dead space has the volume $V_D$. The actual tidal volume $Tid_{Vol,ist}$ shall generate the required alveolar minute volume $V'_{A,req}$ and depends on the actual ventilation frequency $f_{ist}$ and the dead space volume $V_D$.

According to the relationship (17), the inhalation time $T_i$ and thus the duration of a ventilation stroke depend on the actual ventilation frequency $f_{ist}$ and on the ratio D1 as follows:

$$T_i = \frac{D1}{f_{ist}} \quad (33)$$

It is possible to calculate the set tidal volume $Vol_{Tid,set}$ by converting the relationship (1) as follows:

$$Vol_{Tid,set} = \frac{V'_{A,req}}{f_{set}} + V_D \quad (34)$$

The set tidal volume $Vol_{Tid,set}$ is, by contrast, calculated according to the following calculation rule in one embodiment, which leads to a greater set tidal volume $Vol_{Tid,set}$ and depends on the duration $T_i$ of an inhalation process and on the lung time constant $\tau$:

$$Vol_{Tid,set} = \frac{\frac{V'_{A,req}}{f_{set}} + V_D}{1 - e^{-\frac{T_i}{RC}}} = \frac{\frac{V'_{A,req}}{f_{set}} + V_D}{1 - e^{-\frac{T_i}{\tau}}} \quad (35)$$

Figure 8:
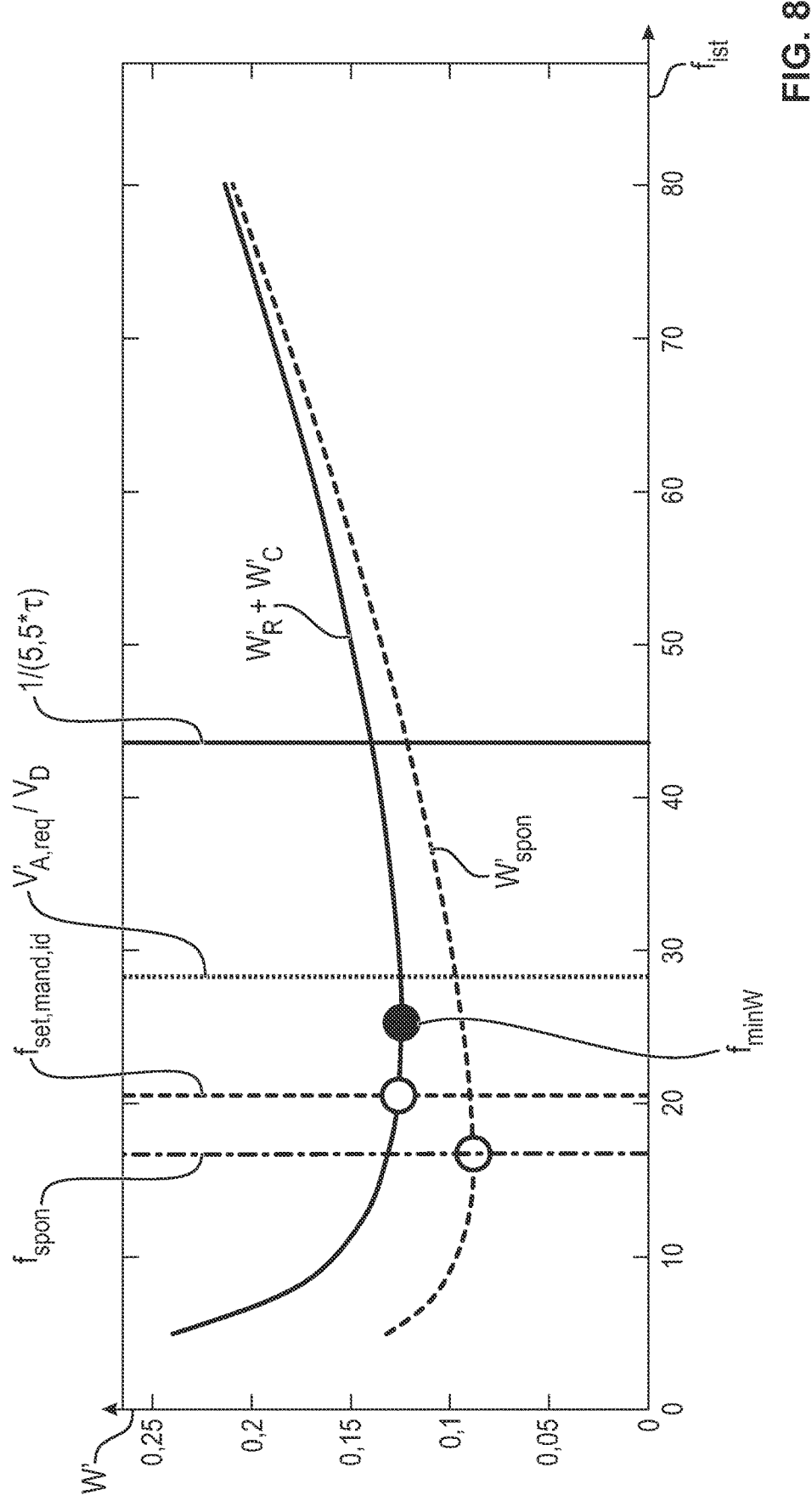
FIG. 8 is a graph showing the overall mechanical power as well as the power for intrinsic breathing activity as a function of the ventilation frequency.

FIG. 8 illustrates the specification of the ventilation frequency set point $f_{set}$. The following parameters were predefined or measured in this example:
The ideal body weight $Gew_{id}$ of the patient P is 75 kg.
The factor x is 5.5. As a reminder: $f_{set,mand} \Leftarrow 1/(x*\tau)$.
The required alveolar minute volume $V'_{A,req}$ is 5.1 L/min.
The volume of the dead space is 2.2 mL/kg.
The compliance C of the lungs Lu is 50 mL/mbar.
The resistance R of the lungs Lu is 5 mbar*sec/L.
Thus, the lung time constant $\tau = R*C = 250$ msec.
The actual ventilation frequency $f_{ist}$ in [1/min] is plotted on the x axis and the resulting power in [W] is plotted on the y axis in FIG. 8.

The ideal mandatory ventilation frequency set point $f_{set,mand,id}$ is deduced according to the calculation rule (21), which leads to a value $f_{set,mand,is} = 21$/min. This value is above the ideal frequency $f_{spon}$ for the intrinsic breathing activity ($f_{spon} = 17$/min) and below the upper threshold $f_{set,mand,max}$ for the mandatory ventilation frequency set point because $V'_{A,req}/V_D = 28$/min and $1/(x*\tau) = 43$/min. Thus, the specification $f_{set,mand} = f_{set,mand,id} = 21$/min is made according to the calculation rule (32).

In addition, the ventilation frequency $f_{minW}$, which leads to a minimal overall power $W'_R + W'_C$, is plotted in FIG. 8. This ventilation frequency $f_{minW}$ can be calculated by a minimization. As was already explained, the process according to the present invention spares such a minimization. As can be seen, the ventilation frequency $f_{minW}$ for the minimal power is greater than the ideal mandatory ventilation frequency set point $f_{set,mand,id}$.

An exemplary procedure for automatically calculating values for different parameters in the case of mechanical ventilation is explained below. This procedure comprises the following steps:
The factors α and x for the mandatory ventilation as well as the factor γ for the set ramp time $t_{R,set}$ and the inhalation portion D1 are predefined, for example, in that they are entered and stored in the ventilator 1.
A desired alveolar minute volume $V'_{A,req}$ or proximal minute volume is determined and predefined in the procedure.
The entire dead space volume $V_D = V_{D,Pat} + V_{D,Ger}$ is determined. The volume $V_{D,Pat}$ of the patient-side dead space is measured approximately by means of the CO2 sensor, for example, by applying Bohr's formula. Or it is estimated by means of the relationship (4). The volume $V_{D,Ger}$ of the device-side dead space is known with sufficient accuracy or is negligibly small due to the construction of the ventilator 1 and to the connection to the patient P.
The mechanical ventilation by the ventilator 1 is started.
The lung time constant τ of the patient P is measured, for which the already mentioned volume flow sensor 2, 15 as well as at least one of the pressure sensors 2, 3, 7 are preferably used.

A set ramp time $t_{R,set}$ for the pressure increase during a ventilation stroke is calculated, for example, according to the calculation rule (16).

The factor SML, i.e., the portion of the desired alveolar minute volume $V'_{A,req}$, which the patient P himself applies by his intrinsic breathing activity, is determined, cf. the relationship (26). For example, the factor SML is determined according to the relationship (29) or by means of the measuring probe 3, which measures the esophageal pressure $P_{es}$.

An ideal frequency $f_{spon}$ of the intrinsic breathing activity of the patient P is calculated, for example, according to the calculation rule (30).

A ventilation frequency set point $f_{set,mand}$, which takes into consideration the intrinsic breathing activity of the patient P, is calculated, preferably according to the calculation rule (31).

The duration $T_i$ of an inhalation process and thus the duration $T_i$ of a ventilation stroke are calculated, namely preferably according to the calculation rule (33).

A set tidal volume $Vol_{Tid,set}$ is specified, preferably according to the calculation rule (35).

A time course of the set pressure $P_{set}$, which the ventilator 1 shall achieve, results from the ventilation frequency set point $f_{set,mand}$ calculated according to the present invention, from the specified set tidal volume $Vol_{Tid,set}$, from the deduced set ramp time $t_{R,set}$ and from the predefined inhalation portion D1.

A lower-level regulation or control is carried out with the goal that the actual curve of the achieved pressure, for example, measured as airway pressure $P_{aw}$, is equal to the curve of the pressure $P_{set}$.

In one embodiment, the calculated ventilation frequency set point $f_{set}$ and the specified set tidal volume $Vol_{Tid,set}$ are shown on the display and operating unit 12. A user can confirm these values or overwrite a displayed value by a manually entered value.

While specific embodiments of the invention have been shown and described in detail to illustrate the application of the principles of the invention, it will be understood that the invention may be embodied otherwise without departing from such principles.

LIST OF REFERENCE NUMBERS

| | |
|---|---|
| 1 | Ventilator; it ventilates the patient P mechanically; it comprises the display and operating unit 12 and the signal processing unit 10 |
| 2 | Pneumatic sensor in front of the mouth of the patient P; it measures the airway pressure $P_{aw}$ and optionally the volume flow Vol'; it acts as the airway pressure sensor; it comprises the components 2.1 and 2.2 |
| 2.1 | Transducer of the sensor 2; it takes a sample of gas from the fluid connection between the lungs Lu of the patient P and the ventilator 1 |
| 2.2 | Pressure sensor proper of the sensor 2 |
| 3 | Probe in the esophagus Sp of the patient; it measures the esophageal pressure $P_{es}$ and optionally the gastric pressure $P_{ga}$; it is connected to the measuring catheter 6 |
| 4 | Connection piece in the mouth of the patient P; it is connected to the measuring catheter 6 in the esophagus Ep |
| 5.1.1, 5.1.2 | Pericardial pair of measuring electrodes on the skin of the patient P |
| 5.2.1, 5.2.2 | Peridiaphragmatic pair of measuring electrodes on the skin of the patient P |
| 6 | Measuring catheter in the esophagus Sp of the patient; it is connected to the measuring probe 3 and to the connection piece 4 |
| 7 | Gastric probe in the stomach Ma of the patient P; it measures the gastric pressure $P_{ga}$ |
| 10 | Data processing signal processing unit; it receives signals from the sensors 2, 3, 5.1.1 through 5.2.2, 15; it calculates a ventilation frequency set point $f_{set}$ |
| 11 | Memory, in which a value indicative of a desired volume flow into the lungs Lu of the patient P is stored |
| 12 | Display and operating unit of the ventilator 1 |
| 15 | Sensor at the ventilator 1; it measures the volume flow Vol' |
| α | Factor, by which the resistive power $W'_R$ shall be greater than the elastic power $W'_C$ |
| C | Compliance of the lungs Lu of the patient P, equal to $Vol/\Delta P$ |
| D1 | $D1 = T_i/(T_i + T_e)$, inhalation time portion of the inhalation process during a ventilation process |
| $f_{ist}$ | Actual frequency of the intrinsic breathing activity or the mechanical ventilation of the patient P |
| E | Elasticity of the lungs, reciprocal of the compliance C |
| $f_{minW}$ | Ventilation frequency, which leads to a minimal overall power $W'_R + W'_C$ |
| $f_{set}$ | Calculated ventilation frequency set point for a mechanical ventilation of the patient P; it contains a $f_{set,\,mand}$ component for the mandatory ventilation and a component that is dependent on $f_{spon}$ for the assisted breathing |
| $f_{set,\,mand}$ | Ventilation frequency set point for a mandatory ventilation in order to achieve a desired alveolar minute volume $V'_{A,\,req}$; it is calculated automatically |
| $f_{set,\,mand,\,id}$ | Ideal mandatory ventilation frequency set point; it depends on the factor α |
| $f_{set,\,mand,\,max}$ | Upper threshold for the mandatory ventilation frequency set point |
| $f_{spon}$ | Ideal frequency of the spontaneous breathing activity of the patient P in order to achieve the desired alveolar minute volume $V'_{A,\,req}$ |
| γ | Factor for specifying the set ramp time $t_{R,\,set}$ |
| $Gew_{id}$ | Ideal body weight of the patient P |
| Ma | Stomach of the patient P |
| $n_{spon}$ | Number of ventilation strokes, which are triggered by the spontaneous breathing activity of the patient P within a period of time |
| $n_{ges}$ | Total number of ventilation strokes performed in this period of time |
| P | Patient, who is mechanically ventilated by the ventilator 1, has the lungs Lu, the stomach Ma, the esophagus Sp and the diaphragm Zw |

| | |
|---|---|
| $P_{set}$ | Desired time course of the pressure, which is achieved by a ventilation stroke of the ventilator 1 during an inhalation process |
| $PTP_{Pat}$ | Value indicative of the mean pressure, which the intrinsic breathing activity of the patient P generates during an inhaled breath |
| $PTP_{Vent}$ | Value indicative of the mean pressure, which the mechanical ventilation of the ventilator 1 generates during an inhaled breath |
| $PV_{aw}$ | Pressure-volume curve, which the diaphragm Zw and the ventilator 1 together apply |
| $PV_{es}$ | Pressure-volume curve, which the diaphragm Zw applies |
| R | Pneumatic resistance of the lungs Lu of the patient, equal to $\Delta P/Vol'$ |
| SML | Factor, which indicates the portion of the alveolar minute volume $V'_{A, spon}$, which is applied by the intrinsic breathing activity of the patient P, at the overall desired alveolar minute volume $V'_{A, req}$ |
| Sp | Esophagus of the patient P; it optionally accommodates the probe 3 |
| $\tau$ | Lung time constant, determined as the product $R*C$ |
| $T_e$ | Duration of the exhalation (exhalation) |
| $T_i$ | Duration of the inhalation (inhalation), at the same time duration of a ventilation stroke |
| TL | Separation line, which runs through the intersection of $PV_{es}$ and $PV_{aw}$ or through the intersection of $P_{es}$ and $P_{aw}$ |
| $t_{R, ist}$ | Achieved ramp time at the beginning of a ventilation stroke, which elapses until the full pressure $P_{set}$ is reached |
| $t_{R, set}$ | Set ramp time, set point for the actual ramp time $t_{R, ist}$ |
| $V'_{A, ist}$ | Actual alveolar minute volume in [L/min], air volume actually flowing into the alveolar lung space of the patient P |
| $V'_{A, req}$ | Desired alveolar minute volume in [L/min] in case of mechanical ventilation, it is predefined |
| $V'_{A, spon}$ | Alveolar minute volume in [L/min], which the patient P achieves due to his own breathing activity |
| $V'_{P, ist}$ | Actual proximal minute volume in [L/min], air volume actually flowing through the mouth of the patient P |
| $V'_{P, req}$ | Desired proximal minute volume in [L/min] in case of mechanical ventilation, it is predefined |
| $V_D$ | Dead space volume in the fluid connection between the lungs Lu of the patient P and the ventilator 1, volume of the dead space, through which air flows during each ventilation stroke, but is not used for exchange with the blood of the patient P, the sum of the device-side dead space volume $V_{D, Ger}$ and the patient-side dead space volume $V_{D, Pat}$ |
| $V_{D, Ger}$ | Device-side dead space volume, volume of the dead space in the area of the fluid connection outside the patient P |
| $V_{D, Pat}$ | Patient-side dead space volume, volume of the dead space in the upper airway and middle airway of the patient P |
| Vol' | Volume flow in the fluid connection, measured by the sensor 3 and/or by the sensor 15 |
| $Vol_{Tid, ist}$ | Actual tidal volume that flows into the breathing system of the patient P during an inhalation process |
| $Vol_{Tid, set}$ | Set tidal volume, which shall be applied into the mouth of the patient P during a breathing cycle; it is essentially equal to the volume, which shall be discharged from the ventilator 1 during a ventilation stroke |
| $W_C$ | Elastic work |
| $W'_C$ | Elastic power |
| $WOB_{Pat}$ | Work applied by the patient P by his own breathing activity during an inhaled breath |
| $WOB_{Vent}$ | Work applied by the mechanical ventilation by the ventilator 1 during an inhaled breath |
| x | Factor for an upper threshold of the mandatory ventilation frequency set point $f_{set, mand}$ |
| $W_{C, exp}$ | Elastic work performed at the end of the exhalation process |
| $W_{C, ins}$ | Elastic work performed at the end of the inhalation process |
| $W_R$ | Resistive (viscose) work |
| $W'_R$ | Resistive power |
| $W_{R, exp}$ | Resistive work performed at the end of an exhalation process |
| $W_{R, ins}$ | Resistive work performed at the end of an inhalation process |
| y | Factor for estimating the volume $V_{D, Pat}$ of the patient-side dead space |
| Zw | Diaphragm of the patient P |

What is claimed is:

1. A process for calculating a ventilation frequency set point as a required ventilation frequency for a ventilator, wherein a fluid connection is configured to be established between a patient's lungs to be mechanically ventilated and the ventilator and wherein the ventilator performs a series of ventilation strokes into the fluid connection as a function of a calculated ventilation frequency set point, the process comprising the steps of:
predefining a value indicative of a desired volume flow into the lungs and out of the lungs of the patient;
determining a lung time constant for the lungs of the patient as a function of measured values of at least one respiratory parameter of the patient;
determining a volume of a dead space in the fluid connection, wherein the dead space occurs in the fluid connection between the ventilator and a region of the lungs of the patient, wherein the which region is suitable for an exchange of gases;
calculating a mandatory frequency set point for a mandatory ventilation of the patient by the ventilator as a function of the predefined desired volume flow value, the determined lung time constant and the determined dead space volume, wherein the calculated mandatory frequency set point is a frequency with which the desired volume flow value is achieved solely by mechanical ventilation;

calculating an ideal spontaneous breathing frequency for an intrinsic breathing activity of the patient as a function of the predefined desired volume flow value, the determined lung time constant and the determined dead space volume, wherein the calculated ideal spontaneous breathing frequency is a frequency with which the patient is capable of achieving the desired volume flow value solely by the patient's own intrinsic breathing activity;

determining a value indicative of an actual intensity of the intrinsic breathing activity of the patient;

calculating the ventilator frequency set point as a weighted average of the calculated mandatory frequency set point and the calculated ideal spontaneous breathing frequency, wherein weighting used in the weighted averaging depends on the determined value indicative of the intrinsic breathing activity, and performing, with the ventilator, a series of ventilation strokes into the fluid connection as a function of the calculated ventilation frequency set point.

2. A process in accordance with claim 1, wherein the step of calculating the mandatory frequency set point comprises the steps of:

predefining a required inhalation portion, wherein the inhalation portion correlates with a time portion of an inhalation process in an overall ventilation process or with a ratio between a duration of an inhalation process and a duration of an exhalation process or both with the time portion of an inhalation process in an overall ventilation process and with the ratio between a duration of an inhalation process and a duration of an exhalation process;

calculating an upper threshold for the mandatory frequency set point as a function of the determined lung time constant;

calculating an ideal mandatory frequency set point as a function of the predefined required inhalation portion; and calculating the mandatory frequency set point using the ideal mandatory frequency set point such that the mandatory frequency set point is smaller than or equal to the calculated upper threshold for the mandatory frequency set point.

3. A process in accordance with claim 2, wherein the step of calculating the ideal mandatory frequency set point comprises the steps of:

predefining a computer-evaluable lung model, which approximately describes a pneumatic behavior of the lungs of a person; and calculating the ideal mandatory frequency set point as a function of the inhalation portion and additionally of a resistive power, wherein according to the lung model the resistive power is to be applied during the mandatory ventilation with the ideal mandatory frequency set point in order to overcome a pneumatic resistance during the filling of the lungs, and of an elastic power wherein according to the lung model the elastic power is to be applied during the mandatory ventilation with the ideal mandatory frequency set point in order to expand the lungs.

4. A process in accordance with claim 3, wherein:
a factor is predefined, which is greater than or equal to 1; and
the ideal mandatory frequency set point is calculated such that during the mandatory ventilation with this frequency, a ratio of the resistive power, which is to be applied according to the lung model during the mandatory ventilation, and the elastic power, which is to be applied according to the lung model during the mandatory ventilation, is equal to the predefined factor.

5. A process in accordance with claim 4, wherein:
a constant is calculated in an initialization phase using the lung model or the constant is calculated in an initialization phase using the lung model and using the factor; and
the ideal mandatory frequency set point is calculated in a subsequent use phase using the predefined inhalation portion, the determined lung time constant, and the calculated constant.

6. A process in accordance with claim 2, wherein the ideal mandatory frequency set point is calculated such that the greater the predefined required inhalation portion is, the greater the ideal mandatory frequency set point is.

7. A process in accordance with claim 2, wherein the upper threshold for the mandatory frequency set point is additionally calculated using the desired volume flow or the determined dead space volume or both the desired volume flow and the determined dead space volume.

8. A process in accordance with claim 1, wherein the mandatory frequency set point for the mandatory ventilation is calculated such that the mandatory frequency set point is greater than or equal to the ideal spontaneous breathing frequency for the intrinsic breathing activity of the patient.

9. A process in accordance with claim 1, wherein the value indicative of the intensity of the intrinsic breathing activity of the patient is determined based on a share of mechanical work or mechanical power, which the intrinsic breathing activity of the patient performs during an inhaled breath wherein the share refers to the overall work or power applied during the inhaled breath.

10. A process in accordance with claim 1, wherein:
a set tidal volume is calculated as a function of the desired volume flow, the determined dead space volume and the calculated ventilation frequency set point;
the set tidal volume being a required value for a volume that the ventilator is to feed into the fluid connection during a ventilation stroke; and
the ventilator is actuated with a control target that the tidal volume generated during at least one ventilation stroke is equal to the calculated set tidal volume.

11. A process in accordance with claim 1, wherein:
for at least one ventilation stroke a required ramp time is determined wherein the required ramp time is a required period of time, which at a beginning of the at least one ventilation stroke shall elapse until a maximum pressure, with which the ventilator performs the at least one ventilation stroke, is reached, the required ramp time being determined as a function of the determined lung time constant; and
the ventilator is actuated with a control target such that an actual ramp time being achieved during at least one ventilation stroke is equal to the determined required ramp time.

12. A process in accordance with claim 1, wherein a computer program which is executable on a signal processing unit carries out at least some of the process steps during an execution of the computer program on the signal processing unit when the signal processing unit receives measured values from a patient sensor configuration, comprising at least one patient sensor, wherein the patient sensor configuration is configured to measure at least one respiratory parameter of the patient.

13. A process in accordance with claim 1, wherein a signal sequence, which is receivable and executable by a signal processing unit brings about at least some of the process steps during an execution on the signal processing unit when the signal processing unit receives measured values from a patient sensor configuration, comprising at least one patient sensor, wherein the patient sensor configuration is configured to measure at least one respiratory parameter of the patient.

14. A signal processing unit for calculating a ventilation frequency set point for a ventilator, wherein a fluid connection is configured to interface with a patient's lungs to be mechanically ventilated and wherein the ventilator is configured to perform a series of ventilation strokes into the fluid connection as a function of the calculated ventilation frequency set point, the signal processing unit comprising:
   memory access to a memory with a stored value indicative of a desired volume flow into the lungs of the patient;
   a processor configuration comprising at least one processor, the processor configuration being configured:
   to receive measured values from a patient sensor configuration comprising at least one patient sensor, wherein the patient sensor configuration is configured to measure at least one respiratory parameter of the patient;
   to determine a lung time constant for the lungs of the patient, as a function of measured values of the patient sensor configuration;
   to determine a volume of a dead space in the fluid connection, wherein the dead space is configured to occur between the ventilator and a region of the lungs of the patient, which wherein the region is suitable for an exchange of gases;
   to calculate a mandatory frequency set point for a mandatory ventilation of the patient by the ventilator as a function of the stored desired volume flow value, the determined lung time constant and the determined dead space volume, wherein the mandatory frequency set point is a frequency with which the desired volume flow value is achieved solely by mechanical ventilation;
   to calculate an ideal spontaneous breathing frequency for an intrinsic breathing activity of the patient as a function of the desired volume flow value, the determined lung time constant and the determined dead space volume, wherein the calculated ideal spontaneous breathing frequency is a frequency with which the patient is capable of achieving the desired volume flow solely by the patient's own intrinsic breathing activity;
   to determine a value indicative of an actual intensity of the intrinsic breathing activity of the patient;
   to calculate the ventilation frequency set point as a weighted average of the mandatory frequency set point and the ideal spontaneous breathing frequency such that the weighting used in the weighted average depends on the determined value of the actual intensity of the intrinsic breathing activity of the patient, and
   to instruct the ventilator to perform a series of ventilation strokes into the fluid connection as a function of the calculated ventilation frequency set point.

15. A signal processing unit in accordance with claim 14, wherein the processor configuration is further configured:
   to read from the memory a predefined required inhalation portion, wherein the inhalation portion correlates with a time portion of an inhalation process in an overall ventilation process or with a ratio between a duration of an inhalation process and a duration of an exhalation process or both with the time portion of an inhalation process in an overall ventilation process and with the ratio between a duration of an inhalation process and a duration of an exhalation process;
   to calculate an upper threshold for the mandatory frequency set point as a function of the determined lung time constant;
   to calculate an ideal mandatory frequency set point as a function of the predefined required inhalation portion; and
   to calculate the mandatory frequency set point using the ideal mandatory frequency set point such that the mandatory frequency set point is smaller than or equal to the calculated upper threshold for the mandatory frequency set point.

16. A signal processing unit in accordance with claim 15, wherein the processor configuration is further configured:
   to read from the memory a predefined computer-evaluable lung model, which approximately describes a pneumatic behavior of the lungs of a person; and
   to calculate the ideal mandatory frequency set point as a function of the inhalation portion and additionally of a resistive power, wherein according to the lung model the resistive power is to be applied during the mandatory ventilation with the ideal mandatory frequency set point in order to overcome a pneumatic resistance during the filling of the lungs, and of an elastic power wherein according to the lung model the elastic power is to be applied during the mandatory ventilation with the ideal mandatory frequency set point in order to expand the lungs.

17. A ventilator for a mechanical ventilation of a patient, wherein a fluid connection is configured to be establishable or established between a patient's lungs to be mechanically ventilated and the ventilator and wherein the ventilator is at least temporarily connected or connectable to a patient sensor configuration, the patient sensor configuration comprising at least one patient sensor, wherein the patient sensor configuration is configured to measure at least one respiratory parameter of the patient, the ventilator comprising:
   memory access to a memory with a stored value indicative of a desired volume flow into the lungs of the patient, wherein the ventilator is configured:
   to calculate a ventilation frequency set point;
   to perform ventilation strokes into the fluid connection as a function of the calculated ventilation frequency set point;
   to receive measured values from the patient sensor configuration;
   to determine a lung time constant, for the lungs of the patient, as a function of measured values of the patient sensor configuration;
   to determine a volume of a dead space in the fluid connection, wherein the dead space is configured to occur between the ventilator and a region of the lungs of the patient, wherein the region is suitable for an exchange of gases;
   to calculate a mandatory frequency set point for a mandatory ventilation of the patient by the ventilator as a function of the stored desired volume flow value, the determined lung time constant and the determined dead space volume, wherein the mandatory frequency set point is a frequency with which the desired volume flow is achieved solely by mechanical ventilation;
to calculate an ideal spontaneous breathing frequency for an intrinsic breathing activity of the patient as a function of the desired volume flow value, the determined lung time constant and the determined dead space volume, wherein the calculated ideal spontaneous breathing frequency is a frequency with which the patient is capable of achieving the desired volume flow solely by the patient's own intrinsic breathing activity;
to determine a value indicative of an actual intensity of the intrinsic breathing activity of the patient;
to calculate the ventilation frequency set point as a weighted average of the mandatory frequency set point and the ideal spontaneous breathing frequency such that the weighting used in the weighted average depends on the determined value indicative of the actual intensity of the intrinsic breathing activity of the patient; and
to perform a series of ventilation strokes into the fluid connection as a function of the calculated ventilation frequency set point.

\* \* \* \* \*